(12) United States Patent
Borzilleri et al.

(10) Patent No.: US 8,124,768 B2
(45) Date of Patent: Feb. 28, 2012

(54) 4-PYRIDINONE COMPOUNDS AND THEIR USE FOR CANCER

(75) Inventors: Robert M. Borzilleri, New Hope, NJ (US); Zhen-Wei Cai, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/863,697

(22) PCT Filed: Jan. 22, 2009

(86) PCT No.: PCT/US2009/031649
§ 371 (c)(1),
(2), (4) Date: Oct. 12, 2010

(87) PCT Pub. No.: WO2009/094417
PCT Pub. Date: Jul. 30, 2009

(65) Prior Publication Data
US 2011/0034416 A1 Feb. 10, 2011

Related U.S. Application Data

(60) Provisional application No. 61/022,848, filed on Jan. 23, 2008.

(51) Int. Cl.
*C07D 401/12* (2006.01)
*C07D 401/14* (2006.01)
*C07F 9/58* (2006.01)

(52) U.S. Cl. ........... 546/24; 546/194; 546/256; 546/261

(58) Field of Classification Search ........................ None
See application file for complete search history.

(56) References Cited

U.S. PATENT DOCUMENTS

| | | | |
|---|---|---|---|
| 6,143,764 A | 11/2000 | Kubo et al. | |
| 6,355,660 B1 | 3/2002 | Ricks et al. | |
| 6,429,213 B1 | 8/2002 | Xue et al. | |
| 6,498,151 B2 * | 12/2002 | Li et al. | 514/80 |
| 6,521,622 B1 | 2/2003 | Ricks et al. | |
| 6,696,487 B2 | 2/2004 | Gerusz et al. | |
| 6,706,740 B2 | 3/2004 | Ricks et al. | |
| 6,858,626 B2 | 2/2005 | Xue et al. | |
| 7,173,031 B2 | 2/2007 | Borzilleri et al. | |
| 7,348,325 B2 | 3/2008 | Cai et al. | |
| 7,439,246 B2 | 10/2008 | Borzilleri et al. | |
| 7,459,562 B2 | 12/2008 | Borzilleri et al. | |
| 7,732,613 B2 | 6/2010 | Kim | |
| 2003/0082631 A1 | 5/2003 | Gustavsson et al. | |
| 2005/0038035 A1 | 2/2005 | Takasugi et al. | |
| 2005/0245530 A1 * | 11/2005 | Borzilleri et al. | 514/252.02 |
| 2005/0288289 A1 | 12/2005 | Crispino et al. | |
| 2005/0288290 A1 | 12/2005 | Borzilleri et al. | |
| 2006/0009453 A1 | 1/2006 | Geuns-Meyer et al. | |
| 2007/0117802 A1 | 5/2007 | Borzilleri et al. | |
| 2007/0219215 A1 | 9/2007 | Kato et al. | |

FOREIGN PATENT DOCUMENTS

| | | |
|---|---|---|
| EP | 430885 | 6/1991 |
| WO | WO97/17329 | 5/1997 |
| WO | WO01/21596 | 3/2001 |
| WO | WO2005/026124 | 3/2005 |
| WO | WO2006/116713 | 11/2006 |
| WO | WO2009/094427 | 7/2009 |

OTHER PUBLICATIONS

PCT International Search Report and Written Opinion (Jul. 27, 2010).
Henley, et al., Poster Presentation (Abstract #106) at $22^{nd}$ EORTC-NCI-AACR Meeting, Berlin, Germany, Nov. 16-19, 2010.
Borzilleri et al., Poster Presentation (Abstract #96) at $22^{nd}$ EORTC-NCI-AACR Meeting, Berlin, Germany, Nov. 16-19, 2010.
Meijer, et al., "Roscovitine and Other Purines as Kinase Inhibitors. From Starfish Oocytes to Clinical Trials," Accounts of Chemical Research, vol. 36, No. 6, (2003), pp. 417-425.
Ventura, et al., "Protein kinases and phosphatases as therapeutic targets in cancer," Clinical and Translational Oncology, vol. 8, No. 3 (2006), pp. 153-160.
Zhong-Yin Zhang, "Chemical and Mechanistic Approaches to the Study of Protein Tyrosine Phosphatases,", Accounts of Chemical Research, vol. 36, No. 6, (2003), pp. 385-392.

* cited by examiner

*Primary Examiner* — Janet Andres
*Assistant Examiner* — Timothy R Rozof
(74) *Attorney, Agent, or Firm* — Gary D. Greenblatt

(57) ABSTRACT

Disclosed are compounds of Formula (I):

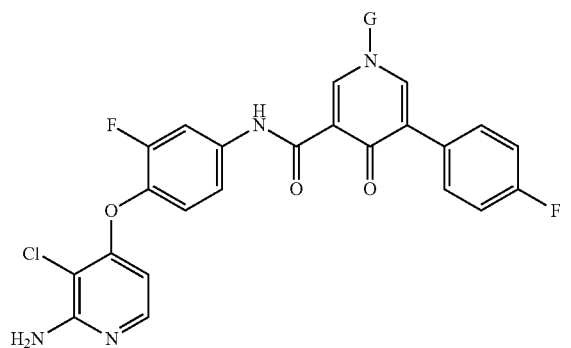

and salts thereof. Also, disclosed are methods of using the compounds in the treatment of proliferative diseases, such as cancer, and to pharmaceutical compositions comprising at least one compound of Formula (I) or a pharmaceutically acceptable salt.

17 Claims, 3 Drawing Sheets

//www.w3.org/1999/xhtml">
4-PYRIDINONE COMPOUNDS AND THEIR USE FOR CANCER

The present invention generally relates to 4-pyridinone compounds and salts thereof, to methods of using such compounds in the treatment of diseases including cancer, and pharmaceutical compositions comprising at least one of said compounds or pharmaceutically acceptable salts thereof.

Met, also referred to as hepatocyte growth factor receptor (HGFR), is expressed predominantly in epithelial cells but has also been identified in endothelial cells, myoblasts, hematopoietic cells and motor neurons. Overexpression of hepatocyte growth factor and activation of Met has been associated with the onset and progression in a number of different tumor types as well as in the promotion of metastatic disease.

U.S. Published Patent Application US 2005/0245530 A1 discloses monocyclic heterocycle compounds that inhibit the protein tyrosine kinase activity of growth factor receptors such as Met, thus making them useful as anti-cancer agents. As may be appreciated, there remains a need for anti-cancer compounds that are useful for treating Met activated cancer and advantageously have activity against other cancer pathways.

Applicants have found a potent compound that has activity against cancers dependent upon Met activation and also has activity against cancers as a VEGFR inhibitor. Applicants have also discovered prodrugs of the compound useful for administration of the compound in a more soluble form. It is now possible to provide compounds with different pharmacological profiles as compared with currently-known anti-cancer compounds for treating Met activated cancers, and that have stability, bioavailability, solubility, therapeutic index and toxicity values that ensure drugability.

BRIEF DESCRIPTION OF THE DRAWINGS

The invention is illustrated by reference to the accompanying drawings described below.

SUMMARY OF THE INVENTION

Figure 1:
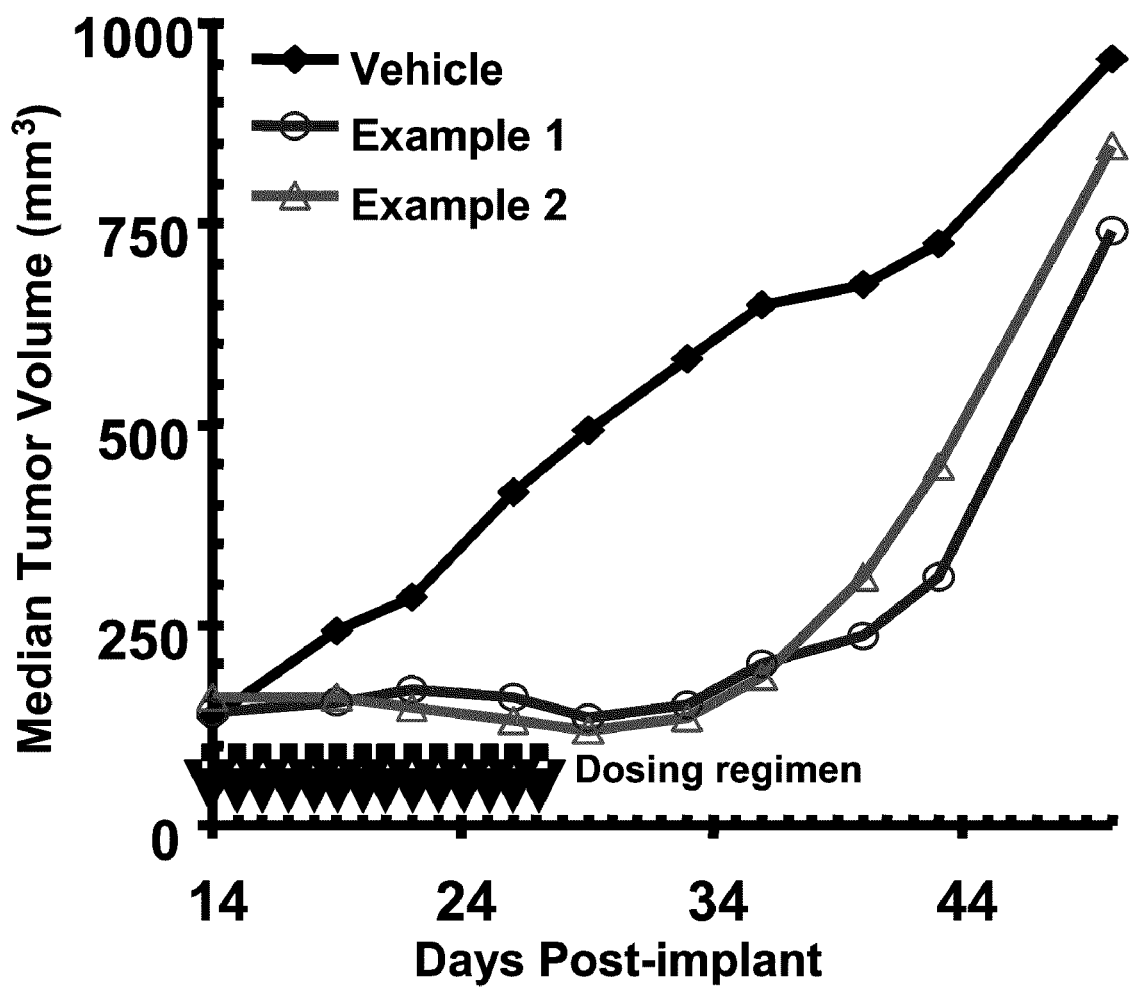
FIG. 1 shows antitumor activities of Example 1 and Example 2 against GTL-16 gastric carcinoma xenografts.

Described are compounds of Formula (I):

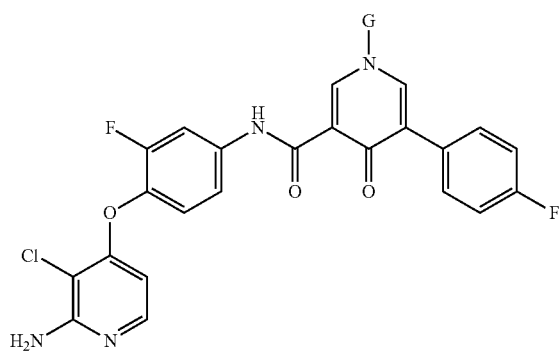

or salts thereof, wherein:

G is H, —CHX—OP(=O)(OH)$_2$, or —CHX—OC(=O)Z;

X is H or alkyl optionally substituted with one or more of OH, halogen, cyano, and/or —NR$^1$R$^2$;

Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl.

Also described are pharmaceutical compositions comprising at least one compound of Formula (I) or a pharmaceutically acceptable salt thereof; and a pharmaceutically acceptable carrier or diluent.

Further described is a method for treating cancer comprising administering to a mammal in need thereof at least one compound of Formula (I) or a pharmaceutically acceptable salt thereof.

DETAILED DESCRIPTION

Listed below are definitions of various terms used to describe the present invention. These definitions apply to the terms as they are used throughout the specification (unless they are otherwise limited in specific instances) either individually or as part of a larger group.

The term "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl, ethyl, propyl, isopropyl, n-butyl, t-butyl, pentyl, hexyl, isohexyl, heptyl, octyl, nonyl, decyl, and dodecyl.

The term "lower alkyl" refers to an "alkyl" and/or "alk" group containing from 1 to 4 carbon atoms and preferably from 1 to 2 carbon atoms, When a subscript is used with reference to an alkyl or other group, the subscript refers to the number of carbon atoms the group may contain. For example, the term "C$_0$-C$_4$alkyl" includes a bond and an alkyl group containing 1 to 4 carbon atoms, and the term "C$_1$-C$_4$alkyl" refers to alkyl groups containing 1 to 4 carbon atoms. Exemplary lower alkyl groups include, but are not limited to, for example, methyl, ethyl, propyl, isopropyl, n-butyl, t-butyl, and isobutyl.

The "alkyl" and/or "alk" group can be optionally substituted with one or more substituents, preferably 1 to 4 substituents, at any available and substitutable position. Exemplary substituents include halogen (e.g., a single halo substituent or multiple halo substituents forming, in the latter case, groups such as, for example, a perfluoroalkyl group or an alkyl group bearing —CCl$_3$ or —CF$_3$), hydroxyl, —NH$_2$, —NH(alkyl), —N(alkyl)$_2$, and cyano.

The term "cycloalkyl" refers to a fully saturated hydrocarbon group containing from 1 to 4 rings and 3 to 8 carbon atoms per ring. Exemplary cycloalkyl groups include, but are not limited to, for example, cyclopropyl, cyclobutyl, cyclopentyl, cyclohexyl, and cycloheptyl. The cycloalkyl group can be optionally substituted with one or more substituents, preferably 1 to 4 substituents, at any available and substitutable point of attachment. Exemplary substituents include those groups recited for substituted alkyl.

The term "aryl" refers to cyclic aromatic hydrocarbon groups having from 1 to 2 aromatic rings, such as, for example, phenyl, biphenyl, or naphthyl. When the aryl group contains two aromatic rings (e.g., bicyclic, etc.), the aromatic rings may be joined at a single point (e.g., biphenyl) or fused (e.g., naphthyl and phenanthrenyl). The aryl group can be optionally substituted with one or more substituents, preferably 1 to 5 substituents, at any available and substitutable ring position, or where valence allows on any rings fused or attached thereto. Exemplary substituents include alkyl and those groups recited for substituted alkyl.

The terms "heterocycle", "heterocyclic" and "heterocyclo" refer to fully saturated, partially saturated, or fully unsaturated, aromatic (i.e., "heteroaryl") or nonaromatic cyclic groups that are, for example, 3 to 7 membered monocyclic or 7 to 11 membered bicyclic ring systems having at least one heteroatom in at least one carbon atom-containing ring. Each ring of the heterocycle, heterocyclic, or heterocyclo containing a heteroatom may have 1, 2, 3, or 4 heteroatoms selected from N, O, and/or S, where the N and/or S heteroatom(s) may optionally be oxidized and the N heteroatom(s) may optionally be quaternized. A heterocycle, heterocyclic, or heterocyclo may be attached to the remainder of the molecule at any heteroatom or carbon atom of the ring or ring system. The heterocycle, heterocyclic, or heterocyclo group can be substituted at any available point of attachment with at least one substituent, preferably 1 to 4 substituents, selected from alkyl and those recited for substituted alkyl.

Exemplary monocyclic heterocycles, heterocyclics, or heterocyclos include, but are not limited to, for example, ethylene oxide; azetidinyl; pyrrolidinyl; pyrrolyl; pyrazolyl; oxetanyl; pyrazolinyl; imidazolyl; imidazolinyl; imidazolidinyl; oxazolyl; oxazolidinyl; isoxazolinyl; isoxazolyl; thiazolyl; thiadiazolyl; thiazolidinyl; isothiazolyl; isothiazolidinyl; furyl; tetrahydrofuryl; thienyl; oxadiazolyl; piperidinyl; piperazinyl; 2-oxopiperazinyl; 2-oxopiperidinyl; 2-oxopyrrolodinyl; 2-oxoazepinyl; azepinyl; hexahydrodiazepinyl; 4-piperidonyl; pyridyl; pyrazinyl; pyrimidinyl; pyridazinyl; triazinyl; triazolyl; tetrazolyl; tetrahydropyranyl; morpholinyl; thiamorpholinyl; thiamorpholinyl sulfoxide; thiamorpholinyl sulfone; 1,3-dioxolane; and tetrahydro-1,1-dioxothienyl.

Exemplary bicyclic heterocycles, heterocyclics, or heterocyclos include, but are not limited to, for example, indolyl; isoindolyl; benzothiazolyl; benzodioxolyl; benzoxazolyl; benzoxadiazolyl; benzothienyl; quinuclidinyl; quinolinyl; tetrahydroisoquinolinyl; isoquinolinyl; benzimidazolyl; benzopyranyl; indolizinyl; benzofuryl; benzofurazanyl; chromonyl; coumarinyl; benzopyranyl; cinnolinyl; quinoxalinyl; indazolyl; pyrrolopyridyl; furopyridinyl, such as, for example, furo[2,3-c]pyridinyl, furo[3,2-b]pyridinyl], and furo[2,3-b]pyridinyl; dihydrobenzodioxinyl; dihydrodioxidobenzothiophenyl; dihydroisoindolyl; dihydroindolyl; dihydroquinolinyl; dihydroquinazolinyl, such as, for example, 3,4-dihydro-4-oxo-quinazolinyl; triazinylazepinyl; and tetrahydroquinolinyl.

The phrase "therapeutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

The compounds of Formula (I) form salts which are also within the scope of this invention. The term "salt(s)" as employed herein, denotes acidic and/or basic salts formed with inorganic and/or organic acids and bases. In addition, when a compound of Formula (I) contains both a basic moiety, such as but not limited to a pyridinyl group, and an acidic moiety such as but not limited to a dihydrogen phosphate group, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparations. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

The phrase "pharmaceutically acceptable salt(s)" as used herein, unless otherwise indicated, includes salts containing pharmacologically acceptable anions or cations, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, sulfate, benzenesulfonate, p-toluenesulfonate and pamoate [i.e., 1,1'-methylene-bis-(2-hydroxy-3-naphthoate)] salts.

Compounds of Formula (I) form salts that can, for example, be used to isolate and/or purify the compounds of Formula (I). Salt(s) of the Formula (I) compounds can be formed by, for example, reacting a Formula (I) compound with, for example, an equivalent amount of acid or base in a medium that allows the thusly formed salt to, for example, either be precipitated out, or be isolated via lyophilization.

Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

The term "prodrug" as employed herein denotes a compound which, upon administration to a subject, undergoes chemical conversion by metabolic or chemical processes to yield the compound of Formula (II) or a salt thereof. Various forms of prodrug(s) are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews,* 8:1-38 (1992).

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of HGF to bind its cognate receptor (Met) in such a way as to activate the receptor that results in a phenotypic response. In the case of Met, this can be cellular proliferation, motility, differentiation and/or survival.

The term "patient" as used herein encompasses all mammalian species, including humans, cows, horses, dogs, and cats; and preferably, humans.

In one embodiment, compounds of Formula (I):

(I)

or salts thereof are provided, wherein:

G is H, —CHX—OP(=O)(OH)$_2$, or —CHX—OC(=O)Z;

X is H or alkyl optionally substituted with one or more of OH, halogen, cyano, and/or —NR$^1$R$^2$;

Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl.

In one embodiment, the compound of Formula (I) or a salt thereof, is provided wherein G is H. The compound of this embodiment has the structure represented by Formula (II):

(II)

The compound of Formula (II) may exist in the enol form represented by the formula below:

(II-enol)

As used herein, the terms "compound of Formula (II)" and "compound of Formula (I) wherein G is H" refer to the compound of Formula (II) in the keto form, the enol form, or any mixture comprising the keto and the enol forms.

In another embodiment, the compound of Formula (II) is provided as a salt. Examples of salts of the compound of Formula (II) include, but are not limited to, trifluoroacetic acid and hydrochloric acid salts.

In one embodiment, compounds of Formula (I) or salts thereof are provided, wherein:

G is —CHX—OP(=O)(OH)$_2$ or —CHX—OC(=O)Z;

X is H or alkyl optionally substituted with one or more of OH, halogen, cyano, and/or —NR$^1$R$^2$;

Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl.

Preferably, X is H or methyl. The compounds or salts thereof of this embodiment are useful as prodrugs of the compound of Formula (II). Upon administration to a mammal, compounds of this embodiment or pharmaceutically acceptable salts thereof, undergo chemical conversion in vivo by metabolic or chemical processes to yield the compound of Formula (II).

In one embodiment, the compounds of Formula (I) or salts thereof, are provided wherein G is —CHX—OP(=O)(OH)$_2$; X is H or C$_1$-C$_4$alkyl optionally substituted with one or more of OH, halogen, cyano, and/or —NR$^1$R$^2$; and R$^1$ and R$^2$ are independently H and/or alkyl. The compounds of this embodiment have the structure of Formula (III):

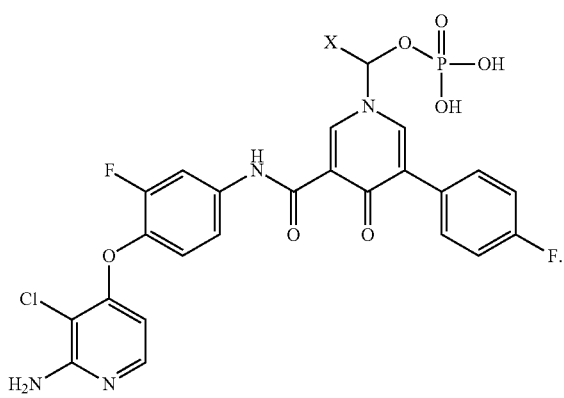

(III)

Preferably, X is H, methyl, substituted methyl, ethyl, or substituted ethyl; more preferably, X is H or methyl, and most preferably X is H. The compounds of Formula (III) may be provided as pharmaceutically acceptable salts, for example, ethanolamine, bis-ethanolamine, trisamine, bis-trisamine, or N-methyl-D-glucamine salts. An example of a compound of Formula (III) is the compound of Formula (IIIa):

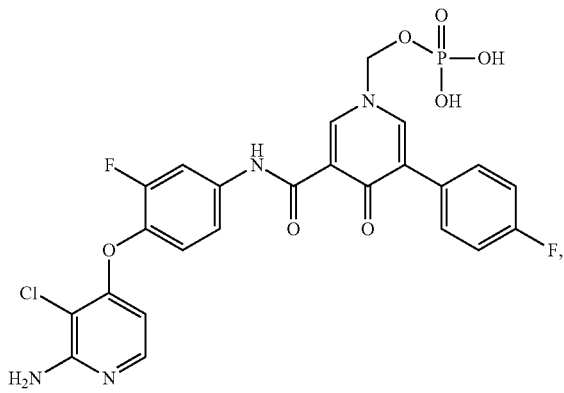

(IIIa)

which may be provided as a salt. Suitable salts of the compound of Formula (IIIa) include, but are not limited to, ethanolamine, bis-ethanolamine, trisamine, and bis-trisamine salts. The compounds of Formula (III) or salts thereof of this embodiment are useful as prodrugs of the compound of Formula (II).

In one embodiment, the compounds of Formula (I) or salts thereof, are provided wherein: G is —CHX—OC(=O)Z; X is H or alkyl optionally substituted with one or more of OH, halogen, cyano, and/or —NR$^1$R$^2$; Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl. Preferably, X is H, C$_1$-C$_4$alkyl, or substituted C$_1$-C$_4$alkyl; more preferably, H, methyl, ethyl, substituted methyl, or substituted ethyl; and most preferably, H or methyl. Preferably, Z is C$_1$-C$_6$alkyl, substituted C$_1$-C$_6$alkyl, C$_3$-C$_6$cycloalkyl, substituted C$_3$-C$_6$cycloalkyl, substituted phenyl, optionally substituted monocyclic or bicyclic heterocyclo. More preferably, Z is C$_1$-C$_6$alkyl substituted with —NH$_2$ or 5- to 6-membered heterocyclo comprising one nitrogen heteroatom, such as pyrrolidinyl and piperidinyl groups. The compounds of Formula (II) or salts thereof of this embodiment are useful as prodrugs of the compound of Formula (II).

In another embodiment, the compounds of Formula (I) or salts thereof, are provided wherein G is:

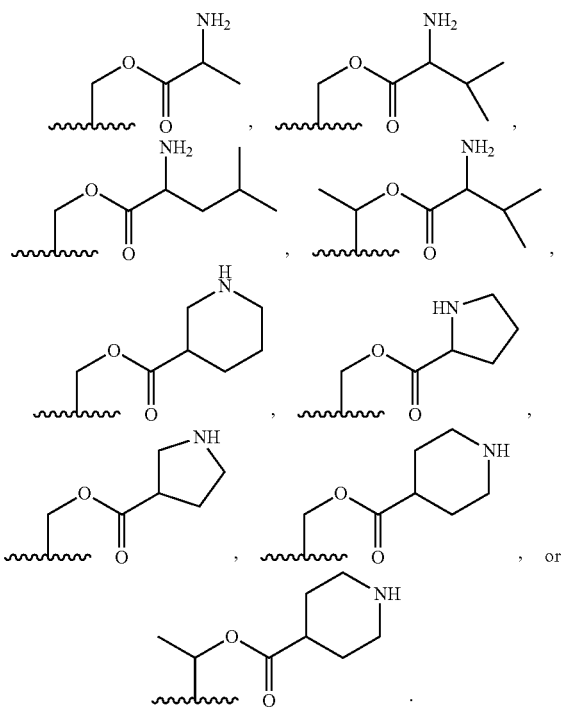

The compounds of this embodiment may be provided as salts. The compounds or salts thereof of this embodiment are useful as prodrugs of the compound of Formula (II).

In one embodiment, a compound of Formula (I) or a salt thereof is provided said compound is:
N-(4-(2-Amino-3-chloropyridin-4-yloxy)-3-fluorophenyl)-5-(4-fluorophenyl)-4-oxo-1,4-dihydropyridine-3-carboxamide (1);
(3-(4-(2-Amino-3-chloropyridin-4-yloxy)-3-fluorophenylcarbamoyl)-5-(4-fluorophenyl)-4-oxopyridin-1(4H)-yl) methyl dihydrogen phosphate (2);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-aminopropanoate (3);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-amino-3-methylbutanoate (4);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-amino-4-methylpentanoate (5);
(3-(4-(2-amino-3-chloropyridin-4-yloxy)-3-fluorophenylcarbamoyl)-5-(4-fluorophenyl)-4-oxopyridin-1(4H)-yl) methyl piperidine-3-carboxylate (6);
(S)-(3-(4-(2-amino-3-chloropyridin-4-yloxy)-3-fluorophenylcarbamoyl)-5-(4-fluorophenyl)-4-oxopyridin-1(4H)-yl)methylpyrrolidine-2-carboxylate (7);
(S)-(3-(4-(2-amino-3-chloropyridin-4-yloxy)-3-fluorophenylcarbamoyl)-5-(4-fluorophenyl)-4-oxopyridin-1(4H)-yl)methylpyrrolidine-3-carboxylate (8);
(3-(4-(2-amino-3-chloropyridin-4-yloxy)-3-fluorophenylcarbamoyl)-5-(4-fluorophenyl)-4-oxopyridin-1(4H)-yl) methyl piperidine-4-carboxylate (9);

1-(3-(4-(2-amino-3-chloropyridin-4-yloxy)-3-fluorophenylcarbamoyl)-5-(4-fluorophenyl)-4-oxopyridin-1(4H)-yl)ethyl piperidine-4-carboxylate (10);

(2S)-1-(3-(4-(2-amino-3-chloropyridin-4-yloxy)-3-fluorophenylcarbamoyl)-5-(4-fluorophenyl)-4-oxopyridin-1(4H)-yl)ethyl 2-amino-3-methylbutanoate (11); or (3-(4-(2-Amino-3-chloropyridin-4-yloxy)-3-fluorophenylcarbamoyl)-5-(4-fluorophenyl)-4-oxopyridin-1(4H)-yl) methyl 1-methylpiperidine-4-carboxylate (12).

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.*, 123:223-235 (1993); Matsumato et al., *Crit. Rev. Oncog.*, 3:27-54 (1992); and Stoker et al., *Nature*, 327:239-242 (1987)). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell*, 67:901-908 (1991)), and promotion of invasion (Stella et al., *Int. J. Biochem. Cell Biol.*, 12:1357-1362 (1999) and Stuart et al., *Int. J. Exp. Path.*, 81:17-30 (2000)), all critical processes underlying metastasis. HGF has also been reported to promote angiogenesis (Bussolino et al., *J. Cell Biol.*, 119:629-641 (1992)). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA*, 84:6379-6383 (1987) and Bottaro et al., *Science*, 251:802-804 (1991)). The mature form of Met consists of a highly glycosylated external $\alpha$-subunit as well as a $\beta$-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene*, 19:5582-5589 (2000)). These include the p85 subunit of the PI3-kinase, phospholipase C$\gamma$ (Gaul et al., *Oncogene*, 19:1509-1518 (2000)), Grb2 and Shc adaptor proteins, the protein phosphatase SHP2 and Gab 1. The latter adapter has emerged as the major downstream docking molecule that becomes tyrosine phosphorylated in response to ligand occupancy (Schaeper et al., *J. Cell Biol.*, 149:1419-1432 (2000); Bardelli et al., *Oncogene*, 18:1139-1146 (1999) and Sachs et al., *J. Cell Biol.*, 150:1375-1384 (2000)). Activation of other signaling molecules has been reported in HGF stimulated cells, most notably Ras, MAP kinases, STATs, ERK-1, -2 and FAK (Tanimura et al., *Oncogene* 17:57-65 (1998); Lai et al., *J. Biol. Chem.*, 275:7474-7480 (2000) and Furge et al., *Oncogene*, 19:5582-5589 (2000)). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-526 (1999)). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-7355 (2003); Lee et al., *Oncogene*, 19:4947-4953 (2000) and Direnzo et al., *Clin. Cancer Res.*, 1:147-154 (1995)). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al., *Cancer Res.*, 55:1963-1970 (1995); Rong et al., *Cancer Res.*, 53:5355-5360 (1993); Kenworthy et al., *Br. J. Cancer*, 66:243-247 (1992) and Scarpino et al., *J. Pathology*, 189:570-575 (1999)). TPR-Met (an activated form similar to BCR/Abl in CML) has been described and identified in human gastric carcinoma (*Proc. Natl. Acad. Sci. USA*, 88:4892-4896 (1991)). In patients with invasive breast carcinoma and in a recent study in non small cell lung cancer patients, expression of either the receptor or ligand is a predictor of decreased survival, further linking Met to tumor progression (Camp et al., *Cancer*, 86:2259-2265 (1999) and Masuya et al., *Br. J. Cancer*, 90:1555-1562 (2004)). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *Proc. Natl. Acad. Sci. USA*, 94:701-706 (1997)) and an amplified/overexpressed Met spontaneously transforms NIH-3T3 cells (Cooper et al., *EMBO J.*, 5:2623-2628 (1986)).

Biological agents, such as ribozymes, antibodies and antisense RNA targeting either HGF or Met have been shown to inhibit tumorogenesis (Stabile et al., *Gene Therapy*, 11:325-335 (2004); Jiang et al., *Clin. Cancer Res*, 9:4274-4281 (2003) and Genentech U.S. Pat. No. 6,214,344 (2001)). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

The compound of Formula (II) is useful for the treatment of cancer, for example, cancers dependent upon Met activation. Met activation is regulated by gene amplification, an activated Met mutation and/or HGF stimulation. Thus, the treatment comprises administering to the patient the compound of Formula (II) or a pharmaceutically acceptable salt or prodrug thereof. It has been found that the compound of Formula (II) is especially useful for treating cancer because of increased potency over known Met kinase inhibitors. Further, the compound of Formula (II) is especially useful for treating cancer because it also has activity as a VEGFR (vascular endometrial growth factor receptor) inhibitor, such as a VEGFR-2 inhibitor.

In one embodiment, a method is provided for treating cancer comprising administering to a mammal in need thereof a compound of Formula (I) or a pharmaceutically acceptable salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, malignant fibrous histiocytoma (MFH), fibrosarcoma, glioblastomas/astrocytomas, melanoma, and mesothelioma. Preferably, the method of this embodiment is used to treat lung cancer, head and neck cancer, gastric cancer, or bladder cancer. Compounds suitable for administration in the method of treatment in this embodiment include prodrugs of the compound of Formula (II), such as compounds of Formula (I) in which G is —CHX—OP(=O)(OH)$_2$ or —CHX—OC(=O)Z; X is H or alkyl optionally substituted with one or more of OH, halogen, cyano, and/or —NR$^1$R$^2$; Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl. Preferably, X is H, C$_1$-C$_4$alkyl, or substituted C$_1$-C$_4$alkyl; more preferably, H, methyl, ethyl, substituted methyl, or substituted ethyl; and most preferably, H or methyl. Preferably, the mammal is a human.

In one embodiment, a method is provided for treating cancer comprising administering to a mammal in need thereof the compound of Formula (II) or a pharmaceutically acceptable salt or prodrug thereof. For example, a therapeutically effective amount of the compound of Formula (II) or a pharmaceutically acceptable salt or prodrug thereof may be administered in this method. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, melanoma, mesothelioma, and glioblastomas/astrocytomas. Preferably, the method of this embodiment is used to treat lung cancer, head and neck cancer, gastric cancer, or bladder cancer. Preferably, the mammal is a human.

In one embodiment, a method is provided for treating cancer comprising administering to a mammal in need thereof one or more prodrugs of the compound of Formula (II) or pharmaceutically acceptable salts of said prodrugs. For example, the method may be used to administer a therapeutically effective amount of one or more prodrugs of the compound of Formula (II) or pharmaceutically acceptable salts of said prodrugs. After administration to the mammal, the one or more prodrugs of the compound of Formula (II) undergo chemical conversion in vivo by metabolic or chemical processes to yield the compound of Formula (II). A therapeutically effective amount of one or more prodrugs refers to the amount(s) of administered prodrug(s) needed to provide a therapeutically effective amount of the compound of Formula (II) in vivo. Preferably, one prodrug is administered in the method of this embodiment. More preferably, a therapeutically effective amount of one prodrug is administered in the method of this embodiment. Suitable prodrugs include compounds of Formula (I) in which G is —CHX—OP(=O)(OH)$_2$ or —CHX—OC(=O)Z; X is H or alkyl optionally substituted with one or more of OH, halogen, cyano, and/or —NR$^1$R$^2$; and Z is alkyl, cycloalkyl, aryl, or heterocyclo optionally substituted with one or more of alkyl, OH, halogen, cyano, and/or —NR$^3$R$^4$; and R$^1$, R$^2$, R$^3$, and R$^4$ are independently H and/or alkyl. Preferably, X is H, C$_1$-C$_4$alkyl, or substituted C$_1$-C$_4$alkyl; more preferably, H, methyl, ethyl, substituted methyl, or substituted ethyl; and most preferably, H or methyl. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma. Preferably, the method of this embodiment is used to treat lung cancer, head and neck cancer, gastric cancer, or bladder cancer. Preferably, the mammal is a human.

In one embodiment, a method is provided for treating cancer comprising administering to a mammal in need thereof the compound of Formula (IIIa) or a pharmaceutically acceptable salt thereof. The compound of Formula (IIIa) is a prodrug of the compound of Formula (II). In the present method, a therapeutically acceptable amount of the compound of Formula (IIIa) or a pharmaceutically acceptable salt thereof may be administered. A therapeutically effective amount of the compound of Formula (IIIa) refers to the amount of the administered prodrug needed to provide a therapeutically effective amount of the compound of Formula (II) in vivo. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma. Preferably, the method of this embodiment is used to treat lung cancer, head and neck cancer, gastric cancer, or bladder cancer. Preferably, the mammal is a human. Pharmaceutically acceptable salts of the compound of Formula (IIIa) useful in the method of this embodiment include the bis-ethanolamine salt and the bis-trisamine salt.

In one embodiment, the use of a compound of Formula (I) or a pharmaceutically acceptable salt thereof, in the manufacture of a medicament for the treatment of cancer is provided. Preferably, in the present embodiment, the cancer subject to treatment is bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, melanoma, glioblastomas/astrocytomas, MFH/fibrosarcoma, or mesothelioma.

In one embodiment, a method is provided for treating cancer in a mammal wherein the cancer is dependent upon Met activation, wherein the Met activation is regulated by gene amplification, an activated Met mutation and/or HGF stimulation, comprising administering to the patient a compound of Formula (I) or a pharmaceutically acceptable salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, melanoma, mesothelioma, and glioblastomas/astrocytomas. Preferably, the method of this embodiment is used to treat lung cancer, head and neck cancer, gastric cancer, or bladder cancer. Compounds suitable for administration in the method of treatment in this embodiment include prodrugs of the compound of Formula (II), such as compounds of Formula (I) in which G is —CHX—OP(=O)(OH)$_2$ or —CHX—OC(=O)Z; X is H or alkyl optionally substituted with one or more of OH, halogen, cyano, and/or —NR$^1$R$^2$; and Z is alkyl, cycloalkyl, aryl, or heterocyclo optionally substituted with one or more of alkyl, OH, halogen, cyano, and/or —NR³R⁴; and R¹, R², R³, and R⁴ are independently H and/or alkyl. Preferably, X is H, $C_1$-$C_4$alkyl, or substituted $C_1$-$C_4$alkyl; more preferably, H, methyl, ethyl, substituted methyl, or substituted ethyl; and most preferably, H or methyl. Preferably, the mammal is a human. Preferably, a therapeutically effective amount of the compound of Formula (I) or a pharmaceutically acceptable salt thereof is administered in the method of this embodiment.

In one embodiment, a method is provided for treating cancer in a mammal wherein the cancer is dependent upon Met activation, wherein the Met activation is regulated by gene amplification, an activated Met mutation and/or HGF stimulation, comprising administering to the patient a compound of Formula (II) or a pharmaceutically acceptable salt or prodrug thereof. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma. Preferably, the method of this embodiment is used to treat lung cancer, head and neck cancer, gastric cancer, or bladder cancer. Preferably, the mammal is a human. Preferably, a therapeutically effective amount of the compound of Formula (II) or a pharmaceutically acceptable salt or prodrug thereof is administered in the method of this embodiment.

In one embodiment, a method is provided for treating cancer in a mammal wherein the cancer is dependent upon Met activation, wherein the Met activation is regulated by gene amplification, an activated Met mutation and/or HGF stimulation, comprising administering to the patient one or more prodrugs of the compound of Formula (II) or salts of said prodrugs. After administration to the mammal, the one or more prodrugs of the compound of Formula (II) undergo chemical conversion in vivo by metabolic or chemical processes to yield the compound of Formula (II). A therapeutically effective amount of one or more prodrugs refers to the amount(s) of administered prodrug(s) needed to provide a therapeutically effective amount of the compound of Formula (II) in vivo. Preferably, one prodrug is administered in a therapeutically effect amount in the method of this embodiment. Suitable prodrugs include compounds of Formula (I) in which G is —CHX—OP(=O)(OH)₂ or —CHX—OC(=O) Z; X is H or alkyl optionally substituted with one or more of OH, halogen, cyano, and/or —NR¹R²; and Z is alkyl, cycloalkyl, aryl, or heterocyclo optionally substituted with one or more of alkyl, OH, halogen, cyano, and/or —NR³R⁴; and R¹, R², R³, and R⁴ are independently H and/or alkyl. Preferably, X is H, $C_1$-$C_4$alkyl, or substituted $C_1$-$C_4$alkyl; more preferably, H, methyl, ethyl, substituted methyl, or substituted ethyl; and most preferably, H or methyl. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma. Preferably, the method of this embodiment is used to treat lung cancer, head and neck cancer, gastric cancer, or bladder cancer. Preferably, the mammal is a human.

In one embodiment, a method is provided for treating cancer in a mammal wherein the cancer is dependent upon Met activation, wherein the Met activation is regulated by gene amplification, an activated Met mutation and/or HGF stimulation, comprising administering to the patient a compound of Formula (IIIa) or a pharmaceutically acceptable salt thereof. The compound of Formula (IIIa) is a prodrug of the compound of Formula (II). A therapeutically effective amount of the compound of Formula (IIIa) refers to the amount of the administered prodrug needed to provide a therapeutically effective amount of the compound of Formula (II) in vivo. Preferably, a therapeutically effective amount of the compound of Formula (IIIa) or a pharmaceutically acceptable salt thereof is administered. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma. Preferably, the method of this embodiment is used to treat lung cancer, head and neck cancer, gastric cancer, or bladder cancer. Preferably, the mammal is a human.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof a compound of Formula (I) or a pharmaceutically acceptable salt or prodrug thereof; and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors;

platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of the compound of Formula (I) or pharmaceutically acceptable salts and prodrugs thereof in preparing medicaments for the treatment of cancer, and/or it comprises the packaging of the compound of Formula (I) herein together with instructions that the compound be used in combination with other anti-cancer or cytotoxic agents and treatments for the treatment of cancer. The present invention further comprises combinations of the compound of Formula (I) and one or more additional agents in kit form, e.g., where they are packaged together or placed in separate packages to be sold together as a kit, or where they are packaged to be formulated together.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof.

Separation of diastereoisomers may be achieved by conventional techniques, e.g., by fractional crystallization, chromatography or H.P.L.C. of a stereoisomeric mixture of a compound of the present invention, or a suitable salt or derivative thereof. An individual enantiomer of the compound may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

Also embraced within this invention is a class of pharmaceutical compositions comprising the compound of Formula (I) or a pharmaceutically acceptable salt and prodrug thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt or prodrug thereof; and optionally an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle. Alternate compositions of this invention comprise a compound of the Formula (I) described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The compounds of Formula (I) can be prepared according to the following Schemes 1 to 4. The compounds are synthesized readily using synthetic methods known to one skilled in the art. Solvates (e.g., hydrates and salts) of the compounds described are also within the scope of the present invention. Methods of solvation and salt formation are generally known in the art. Accordingly, the compounds and examples of the instant invention may be in the free or hydrate form, and may be obtained by methods exemplified in the following schemes below.

The compound of Formula (II) can be readily prepared using the synthetic sequence outlined in Scheme 1. The reaction of 2,3-dichloropyridine (2) with diphenylmethanimine (3) in the presence of a catalytic amount of palladium (II) acetate, racemic-BINAP (2,2'-bis(diphenylphosphino)-1,1'-binaphthylene) and cesium carbonate in THF can furnish the benzophenone imine 4. Metallation-borylation-oxidation of intermediate 4 as denoted in Scheme 1 can provide 3-chloro-2-(diphenylmethyleneamino) pyridin-4(1H)-one (5), which can then be immediately treated with 1,2-difluoro-4-nitrobenzene and a base, such as cesium carbonate to afford intermediate 6. Chemoselective reduction of the nitro substituent of intermediate 6 with for example, ammonium sulfide in isopropanol, can provide amine 7. Intermediate 7 can then be coupled to 5-(4-fluorophenyl)-4-oxo-1,4-dihydropyridine-3-carboxylic acid (8) using standard peptide coupling reagents, such as O-(7-azabenzotriazol-1-yl)-N,N,N',N'-tetramethyluronium hexafluorophosphate (HATU) to obtain intermediate 9. Acid-catalyzed hydrolysis of imine 9 can then provide the desired Comound (II).

SCHEME 1

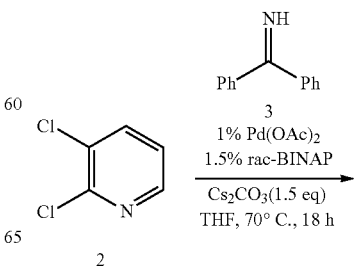

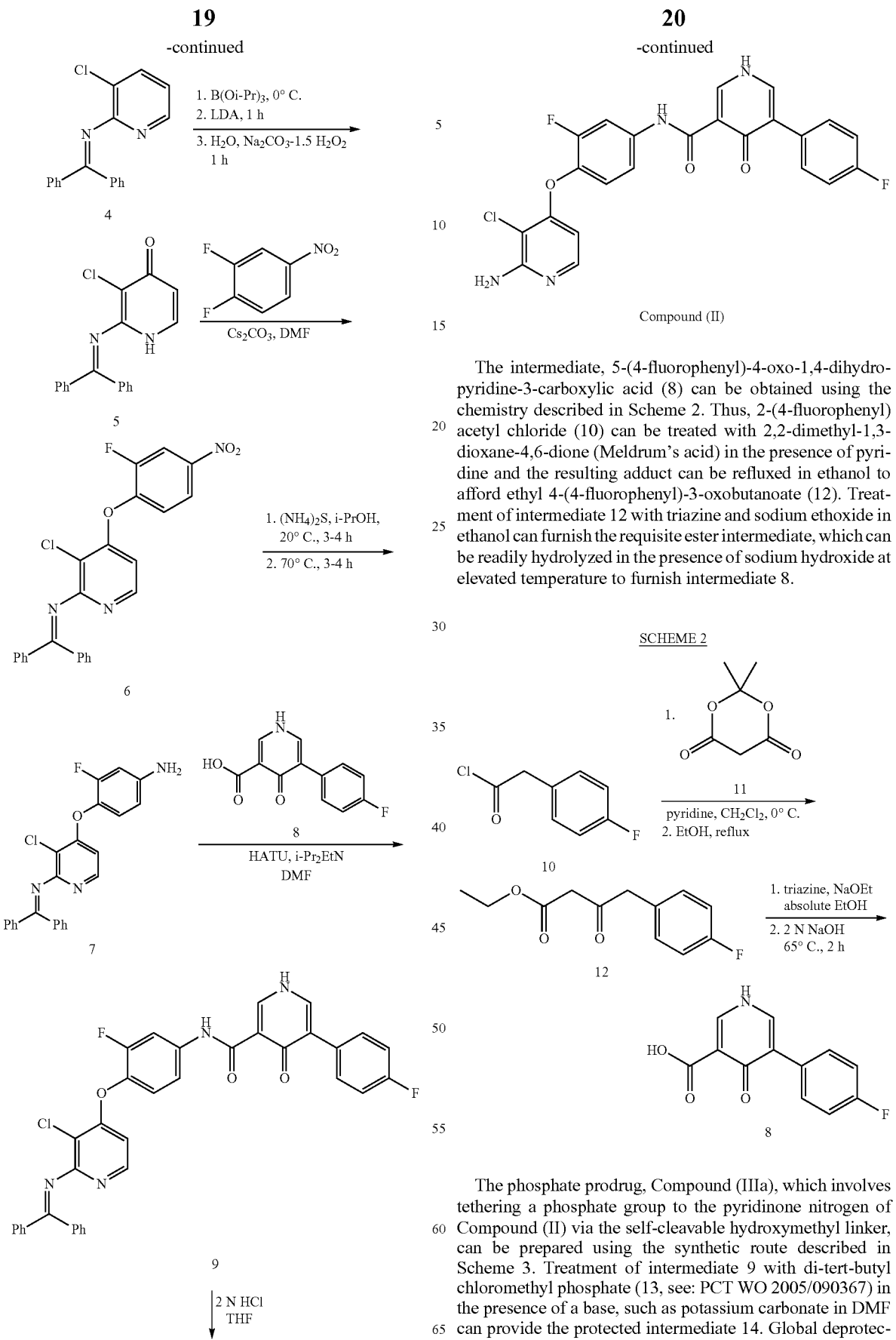

The intermediate, 5-(4-fluorophenyl)-4-oxo-1,4-dihydro-pyridine-3-carboxylic acid (8) can be obtained using the chemistry described in Scheme 2. Thus, 2-(4-fluorophenyl) acetyl chloride (10) can be treated with 2,2-dimethyl-1,3-dioxane-4,6-dione (Meldrum's acid) in the presence of pyridine and the resulting adduct can be refluxed in ethanol to afford ethyl 4-(4-fluorophenyl)-3-oxobutanoate (12). Treatment of intermediate 12 with triazine and sodium ethoxide in ethanol can furnish the requisite ester intermediate, which can be readily hydrolyzed in the presence of sodium hydroxide at elevated temperature to furnish intermediate 8.

The phosphate prodrug, Compound (IIIa), which involves tethering a phosphate group to the pyridinone nitrogen of Compound (II) via the self-cleavable hydroxymethyl linker, can be prepared using the synthetic route described in Scheme 3. Treatment of intermediate 9 with di-tert-butyl chloromethyl phosphate (13, see: PCT WO 2005/090367) in the presence of a base, such as potassium carbonate in DMF can provide the protected intermediate 14. Global deprotection of 14 under acid conditions in ethanol can furnish the desired phosphate prodrug, Compound (IIIa).

SCHEME 3

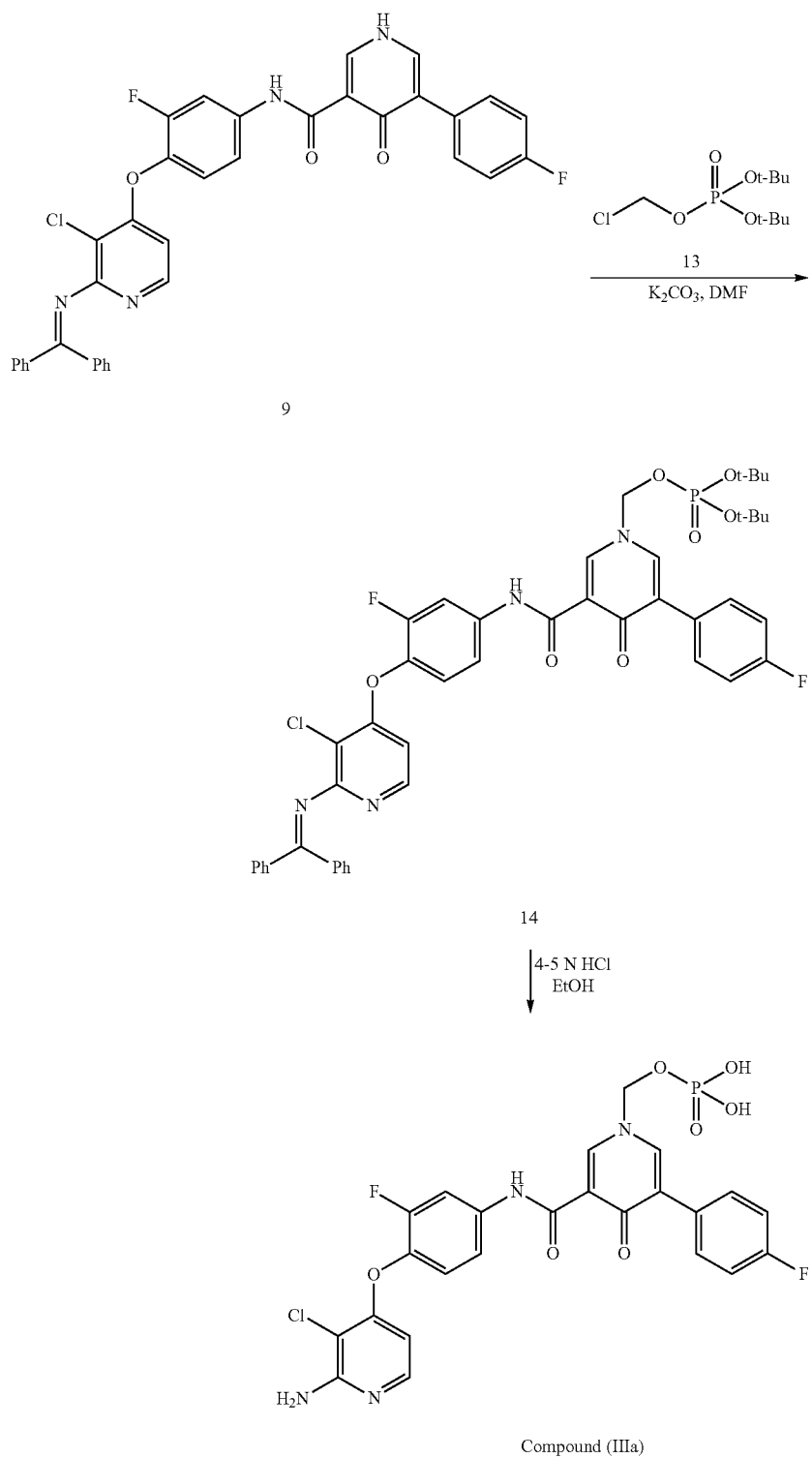

Amino acids can also be tethered to Compound (II) via the hydroxymethyl linker, in a manner similar to that described above using the synthetic sequence illustrated in Scheme 4. The chloromethyl esters 16, derived from the corresponding N-protected amino acids (using the procedures described in *Synth. Commun.*, 14:857-864 (1984) and *Synth. Commun.*, 24:767-772 (1994)) can be reacted with Compound (II) in the presence of a base, such as potassium carbonate to afford intermediate 17. Removal of the nitrogen protecting group, in this case a Boc (t-butyl carbamate) group, under acid conditions can furnish the desired amino acid ester prodrug 18.

SCHEME 4

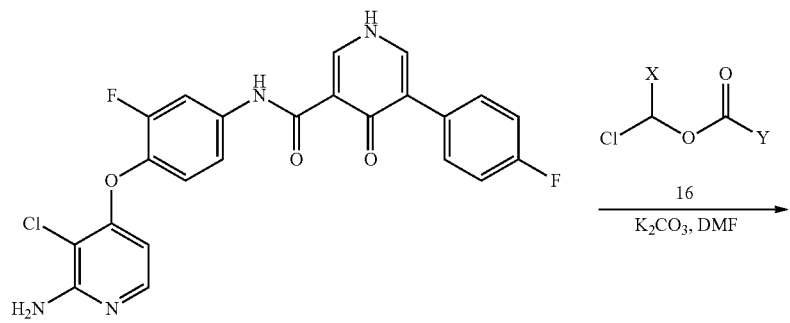

Compound (II)

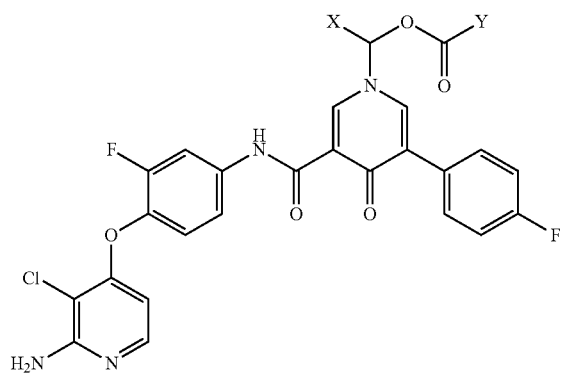

17

TFA
CH$_2$Cl$_2$

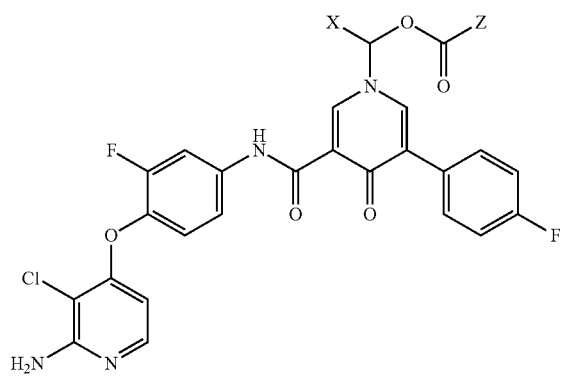

18

H = H, alkyl, or substituted alkyl
Y = N-protected alkyl or cycloalkyl amine
Z = alkyl or cycloalkyl amine

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended thereto.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP)HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP)HPLC was performed with a linear gradient elution using 10% methanol, 90% water, 0.1% TFA (solvent A) and 90% methanol, 10% water, 0.1% TFA (solvent B) and detection at 220 nm on one of the following columns: A—Shimadzu S5 ODS-VP 20×100 mm column with a flow rate of 20 mL/min; B—YMC S5 ODS 30×100 mm column with a flow rate of 20 mL/min; C—Phenomonex 30×250 mm column with a flow rate of 10 mL/min; D—YMC S5 ODS 20×250 mm column with a flow rate of 10 mL/min; E—YMC S10 ODS 50×500 mm column with a flow rate of 50 mL/min; or F—YMC S10 ODS 30×500 mm column with a flow rate of 20 mL/min.

The final product was characterized by $^1$H NMR, RP HPLC, electrospray ionization (ESI MS) or atmospheric pressure ionization (API MS) mass spectrometry. $^1$H NMR spectra were obtained on either a 400 MHz Bruker or a 500 MHz JEOL instrument. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; TEA: triethylamine; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxy-tris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT or rt: room temperature; $t_R$: retention time; h: hour(s); min: minute(s); PyBroP: bromotripyrrolidinophosphonium hexafluorophosphate; HATU: O-(7-azabenzotriazol-1-yl)-N,N,N',N'-tetramethyluronium hexafluorophosphate; TBTU: O-(1H-benzotriazol-1-yl)-N,N,N',N'-tetramethyluronium tetrafluoroborate; DMAP: 4-N,N-dimethylaminopyridine; HOBt or HOBT: hydroxybenzotriazole; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether; DCM: dichloromethane or methylene chloride; m-CPBA: 4-chloroperoxybenzoic acid; racemic-BINAP: 2,2'-bis(diphenylphosphino)-1,1'-binaphthylene.

Example 1

N-(4-(2-Amino-3-chloropyridin-4-yloxy)-3-fluorophenyl)-5-(4-fluorophenyl)-4-oxo-1,4-dihydropyridine-3-carboxamide

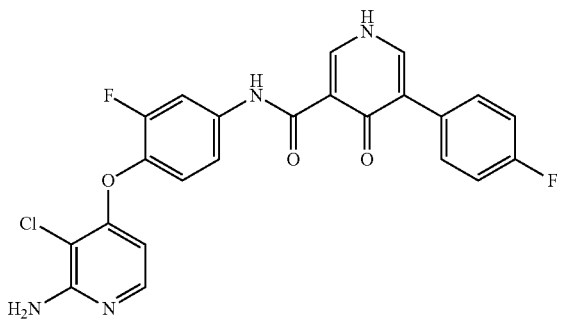

(1)

Preparation 1A:
3-Chloro-N-(diphenylmethylene)pyridin-2-amine

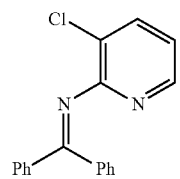

(1A)

2,3-Dichloropyridine (105.00 g, 710 mmol), Pd(OAc)$_2$ (3.98 g, 17.74 mmol), rac-BINAP (16.57 g, 26.61 mmol), cesium carbonate (346.76 g, 1065 mmol), THF (1.05 L), and benzophenone imine (124.67 mL, 745 mmol) were added to a 2 L CHEMGLASS® Reactor fitted with a mechanical stirrer and reflux condenser. The mixture was heated to reflux with stirring for 18 h. The material was filtered, washed with THF (100 mL). The resulting filtrate was concentrated in vacuo to ⅓ volume and used without further purification. $^1$H NMR (CDCl$_3$) δ 6.79 (dd, 1H, J=4.6, 7.6 Hz), 7.19-7.60 (m, 9H), 7.79-7.95 (m, 2H), 8.16 (dd, 1H, J=1.5, 5.1 Hz); MS (ESI$^+$) m/z 293.1 (M+H)$^+$.

Preparation 1B: 3-Chloro-2-(diphenylmethyleneamino)pyridin-4(1H)-one

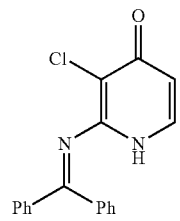

(1B)

To a 4-L CHEMGLASS® reactor (fitted with addition funnel, nitrogen blanket) was added: crude 3-chloro-N-(diphenylmethylene)pyridin-2-amine and triisopropyl borate (196.38 mL, 852 mmol). The resulting solution was the cooled to 0° C. In a separate reactor was added diisopropylamine (169.78 mL, 1207 mmol) and THF (1.05 L). This solution was cooled to 0° C. and n-butyl lithium (683.22 mL, 923 mmol) was added slowly. After stirring at 0° C., this solution was added slowly to the first solution. The reaction mixture was stirred for 30 min without the cooling bath (HPLC indicated consumption of starting material). Water (1.05 L) was added to the mixture, followed by the addition of sodium percarbonate (336.34 g, 1065 mmol) in one portion. This mixture was allowed to stir at 20° C. for 1 h. A saturated solution of NaHSO$_3$ (~1 L) was added slowly. The aqueous layer was removed and DMF (840.00 mL) was added to the organic layer and the THF was distilled off (solvent swap from THF to DMF). The DMF was used without further purification. $^1$H NMR (CDCl$_3$) δ 6.02 (d, 1H, J=7.1 Hz), 7.10 (d, 1H, J=7.1 Hz), 7.20-7.80 (m, 10H); MS (ESI$^+$) m/z 309.07 (M+H)$^+$.

Preparation 1C: 3-Chloro-N-(diphenylmethylene)-4-(2-fluoro-4-nitrophenoxy)pyrdin-2-amine

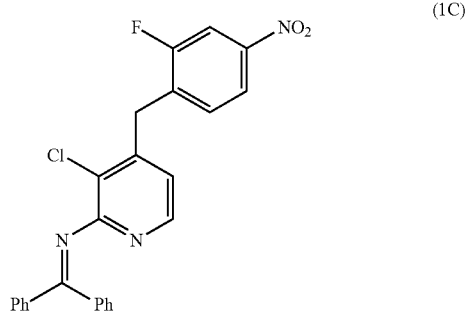

(1C)

To a 2-L CHEMGLASS® reactor was added the crude 3-chloro-2-(diphenylmethyleneamino)pyridin-4(1H)-one (from above, now in DMF) and cesium carbonate (300.52 g, 923 mmol) followed by the addition of 3,4-difluoronitrobenzene (118.15 mL, 1065 mmol). The mixture was heated to approximately 90° C. with stirring for 2 h. The mixture was cooled to 25° C. with stirring for 10 min. To this solution was added water (1 L). The mixture was extracted with EtOAc (1 L) and the aqueous phase was discarded. The organics were concentrated to afford an oil. The oil was dissolved into EtOH (200 mL) (heating sometimes required). After the solution was allowed to stand at 25° C. for 4 h, a solid was collected by filtration to afford 3-chloro-N-(diphenylmethylene)-4-(2-fluoro-4-nitrophenoxy)pyridin-2-amine (104.00 g; 32.73% yield) as a yellow solid. $^1$H NMR (CDCl$_3$) δ 6.52 (d, 1H, J=5.6 Hz), 6.80 (dd, 1H, J=8.1, 9.1 Hz), 7.21-7.60 (m, 8H), 7.78-7.95 (m, 2H), 8.00 (m, 1H), 8.11 (dd, 1H, J=2.5, 9.6 Hz), 8.17 (d, 1H, J=5.6 Hz); MS (ESI$^+$) m/z 448.01 (M+H)$^+$.

Preparation 1D: 4-(4-Amino-2-fluorophenoxy)-3-chloro-N-(diphenylmethylene) pyridin-2-amine

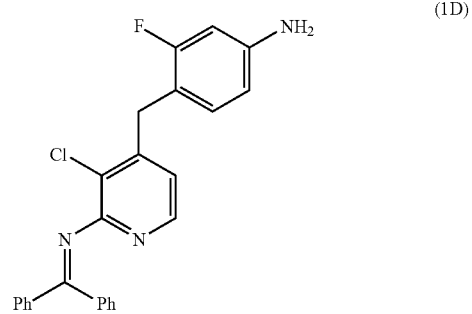

(1D)

The following materials were added to a 2-L CHEMGLASS® reactor: 3-chloro-N-(diphenylmethylene)-4-(2-fluoro-4-nitrophenoxy)pyridin-2-amine (110.00 g, 221 mmol), isopropyl alcohol (990.00 mL), ammonium sulfide (~40% in water, 297.00 mL, 2324 mmol). The mixture was allowed to stir at 20° C. for 3-4 h. 3-Chloro-N-(diphenylmethylene)-4-(2-fluoro-4-nitrophenoxy)pyridin-2-amine was not detected by HPLC analysis. The reaction mixture was heated to 70° C. and allowed to stir for 3-4 h. Once the reaction was complete, water (14 mL/g·LR) was added. The reaction mixture was cooled to 20° C. (reaction temp) over 1 h. Upon cooling a solid precipitated and was filtered off and washed with water (12.5 mL/g·LR), followed by heptane: MTBE (4:1; 5 mL/g·LR). After LOD (~25%), 95.3 g of crude 4-(4-amino-2-fluorophenoxy)-3-chloro-N-(diphenylmethylene)pyridin-2-amine (90AP) was obtained. The crude 4-(4-amino-2-fluorophenoxy)-3-chloro-N-(diphenylmethylene) pyridin-2-amine was dissolved into n-BuOAc (7 mL/g·LR) by heating to approximately 85° C. At 85° C., heptane (7 mL/g·LR) was added dropwise until the solution became cloudy. The solution was then allowed to cool to 20° C. with stirring. Once at 20° C., the slurry was aged for 8 h. The solid was filtered, washed with heptane (5 mL/g·LR), and then dried overnight in a vacuum oven at 60° C. to afford 4-(4-amino-2-fluorophenoxy)-3-chloro-N-(diphenylmethylene) pyridin-2-amine (62.53 g; 67.69% yield) as a faint yellow solid. $^1$H NMR (CDCl$_3$) δ 6.23 (dd, 1H, J=1.0, 5.6 Hz), 6.43 (m, 1H), 6.49 (dd, 1H, J=2.5, 12.1 Hz), 6.92 (t, 1H, J=8.6 Hz), 7.25-7.60 (m, 8H), 7.87 (m, 2H), 7.95 (d, 1H, J=6.1 Hz); MS (ESI$^+$) m/z 418.6 (M+H)$^+$.

Preparation 1E: Ethyl 4-(4-fluorophenyl)-3-oxobutanoate

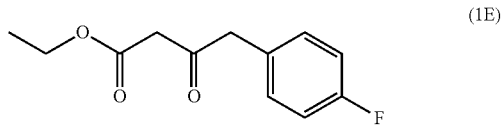

(1E)

To a solution of 2,2-dimethyl-1,3-dioxane-4,6-dione (Meldrum's acid, 8.0 g, 56 mmol) dissolved in anhydrous methylene chloride (100 mL) and pyridine (11 mL), at 0° C. under nitrogen atmosphere, was slowly added 2-(4-fluorophenyl)acetyl chloride (7.6 mL, 9.6 g, 56 mmol). The red solution was stirred at 0° C. for 1.5 h. The reaction mixture was treated with 1 N HCl (13 mL) and diluted with methylene chloride (200 mL). The layers were separated and the organic layer was washed with saturated aqueous sodium chloride, dried and concentrated in vacuo to give 5-(2-(4-fluorophenyl)acetyl)-2,2-dimethyl-1,3-dioxane-4,6-dione. The crude intermediate was suspended in absolute ethanol (150 mL) and the resulting mixture was refluxed for 4 hours. The solvent was then removed in vacuo and the residue was purified by flash column chromatography (SiO$_2$, 230-400 mesh, 8:1 hexane-ethyl acetate gradient elution) to afford the desired product (4.6 g, 37%). $^1$H NMR (CDCl$_3$) δ 7.23-7.15 (m, 2H), 7.05-6.98 (m, 2H), 4.18 (q, 2H, J=7.0 Hz), 3.81 (s, 2H), 3.46 (s, 2H), 1.26 (t, 3H, J=7.0 Hz); MS (ESI$^+$) m/z 225 (M+H)$^+$.

Preparation 1F: 5-(4-Fluorophenyl)-4-oxo-1,4-dihydropyridine-3-carboxylic acid

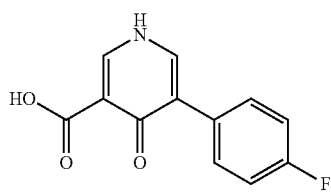

(1F)

To a solution of ethyl 4-(4-fluorophenyl)-3-oxobutanoate (4.6 g, 21 mmol) in absolute ethanol (45 mL) was added NaOEt solution (21% NaOEt solution in EtOH, 7.7 mL) and triazine (1.67 g, 21 mmol). The resulting mixture was heated to 85° C. for 1.5 h, cooled to room temperature and treated with an additional portion of triazine (0.08 g, 1 mmol) and NaOEt solution (21% NaOEt solution in EtOH, 0.4 mL). The reaction mixture was heated for an additional hour and concentrated in vacuo. The residue was treated with 1N HCl until the pH of the reaction was about 2. The precipitate was collected to give the desired ester intermediate, ethyl 5-(4-fluorophenyl)-4-oxo-1,4-dihydropyridine-3-carboxylate (4.5 g, 83%) as a yellow solid. MS (ESI$^+$) m/z 262 (M+H)$^+$.

The above ester (1.0 g, 3.8 mmol) was dissolved in 2N NaOH (20 mL) and heated to 65° C. for 2 h. The resulting clear mixture was cooled to ambient temperature and the solids were filtered off. The filtrate was then acidified with 1N HCl to pH=1 and the resulting yellow precipitate was collected as the desired product (0.73 g, 82%). $^1$H NMR (DMSO-d$_6$) δ 13.52 (br s, 1H), 8.86 (s, 1H), 8.51 (s, 1H), 7.99-7.96 (m, 2H), 7.55-7.51 (m, 2H); MS (ESI$^+$) m/z 234 (M+H)$^+$.

Preparation 1G: N-(4-(3-Chloro-2-(diphenylmethyleneamino)pyridin-4-yloxy)-3-fluorophenyl)-5-(4-fluorophenyl)-4-oxo-1,4-dihydropyridine-3-carboxamide

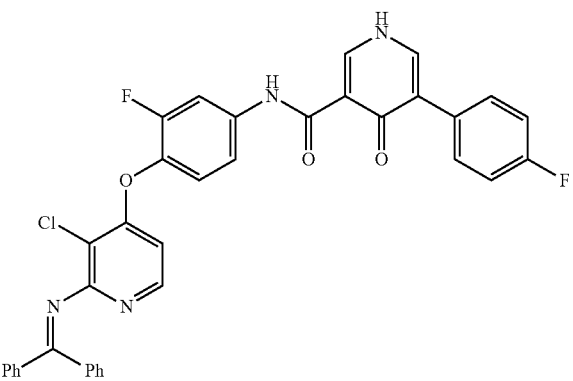

(1G)

To a solution of 4-(4-amino-2-fluorophenoxy)-3-chloro-N-(diphenylmethylene)pyridin-2-amine (836 mg, 2.0 mmol) and 5-(4-fluorophenyl)-4-oxo-1,4-dihydropyridine-3-carboxylic acid (490 mg, 2.0 mmol) in DMF (10 mL) at room temperature were added HATU (913 mg, 2.4 mmol) and DIPEA (1.05 ml, 6.0 mmol). The reaction mixture was stirred at room temperature for 3 h prior to being quenched by the addition of cold water (50 mL). The solid that formed was collected by filtration, and washed with water and ether. The solid was dissolved in DCM and purified by flash column chromatography (SiO$_2$, DCM to 10% MeOH in DCM) to give the desired product (987 mg, 78%) as a light yellow solid. MS (ESI$^+$) m/z 633 (M+H)$^+$.

Example 1

To a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (410 mg, 0.65 mmol) in THF (10 mL) at room temperature was added aqueous HCl (2 M, 0.81 mL, 1.62 mmol). The reaction mixture was stirred at room temperature for 1 h and then concentrated in vacuo. Cold 5% aq. NaHCO$_3$ (5 mL) was then added to the residue. The solid that formed was collected by filtration, washed with water and then ether, and dried under vacuum to give the desired product (275 mg, 90%). $^1$H NMR (DMSO-d$_6$) δ 13.31 (s, 1H), 12.70 (br s, 1H), 8.63 (d, 1H, J=1.30 Hz), 8.09 (d, 1H, J=1.50 Hz), 8.02 (dd, 1H, J=2.50, 13.10 Hz), 7.76 (d, 1H, J=5.50 Hz), 7.71 (m, 2H), 7.44 (dd, 1H, J=1.50, 8.80 Hz), 7.31 (t, 1H, J=8.80 Hz), 7.27 (t, 2 H, J=8.80 Hz), 6.43 (br s, 2H), 5.96 (d, 1H, J=5.60 Hz); MS (ESI$^+$) m/z 469 (M+H)$^+$.

N-(4-(2-Amino-3-chloropyridin-4-yloxy)-3-fluorophenyl)-5-(4-fluorophenyl)-4-oxo-1,4-dihydropyridine-3-carboxamide, hydrochloride salt The HCl salt of N-(4-(2-amino-3-chloropyridin-4-yloxy)-3-fluorophenyl)-5-(4-fluorophenyl)-4-oxo-1,4-dihydropyridine-3-carboxamide (Examples 1) is obtained by treating a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (Preparation 1G) in THF with excess aqueous HCl at room temperature. The volatiles are removed in vacuo to provide the desired compound.

Example 2

(3-(4-(2-Amino-3-chloropyridin-4-yloxy)-3-fluorophenylcarbamoyl)-5-(4-fluorophenyl)-4-oxopyridin-1(4H)-yl)methyl dihydrogen phosphate (2)

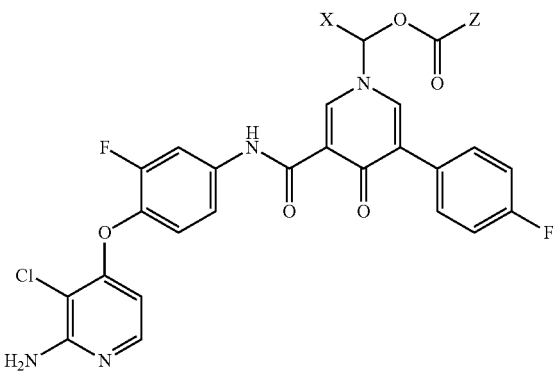

To a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (5.0 g, 7.90 mmol) in DMF (50 mL) at room temperature were added potassium carbonate (7.64 g, 55.3 mmol) and di-tert-butyl chloromethyl phosphate (9.19 g, 35.5 mmol, see: PCT WO 2005/090367). The reaction mixture was stirred at room temperature for 2 days. The mixture was then diluted with EtOAc (250 mL), washed with water (200 mL), aq 10% LiCl (3×250 mL), dried over $Na_2SO_4$, and filtered. The filtrate was concentrated to give a residue, which was dissolved in EtOH (160 mL). To this stirred solution, was added water (60 mL), followed by the slow addition of conc. HCl (40 mL). The resulting mixture was stirred at rt for 15 min, and then allowed to stand overnight. HPLC analysis indicated that the reaction was complete. The solid was collected by filtration, rinsed with 50% $EtOH/H_2O$ (5×), water, EtOH, and EtOAc. The solid was dried under vacuum to give the title compound (4.3 g, 93%) as a white solid. $^1$H NMR (TFA-d) δ 9.60 (s, 1H), 8.79 (s, 1 H), 7.80-7.90 (m, 2H), 7.65-7.75 (m, 2H), 7.57 (d, 1H, J=7.04 Hz), 7.45 (t, 1H, J=6.80 Hz), 7.25-7.33 (m, 2H), 6.50 (d, 1H, J=5.92 Hz), 6.39 (d, 2H, J=9.88 Hz); MS (ESI$^+$) m/z 579 (M+H)$^+$.

Examples 3 to 11

Examples 3 to11 were prepared using the following General Procedure: To a mixture of N-(4-(2-amino-3-chloropyridin-4-yloxy)-3-fluorophenyl)-5-(4-fluorophenyl)-4-oxo-1,4-dihydropyridine-3-carboxamide (Example 1, 0.1 mmol) and potassium carbonate (0.4 mmol) in DMF (1 mL), was added the corresponding chloromethyl ester derivative (0.3 mmol, for preparation, see *Synth. Commun.*, 14:857-864 (1984)). The reaction mixture was stirred at rt for 1-3 h, diluted with DCM, and washed with aq. $KH_2PO_4$ solution. The organic layer was dried over $MgSO_4$ and the N-Boc-protected intermediate was purified by column chromatography ($SiO_2$, using a DCM/EtOAc gradient elution).

The N-Boc-protected intermediate was then treated with 30% TFA/DCM (2 mL) for 1 h. The solvents were removed in vacuo, and the product was purified by preparative-HPLC to afford the title compound as a TFA salt.

TABLE 1

Examples 3 to 11

| Example No. | X | Z | Analytical Data |
|---|---|---|---|
| 3 | H | 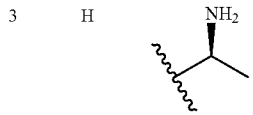 | $^1$H NMR (CD$_3$OD) δ 12.75 (br s, 1H), 8.83 (d, 1H, J = 2.24 Hz), 8.11 (d, 1H, J = 2.52 Hz), 7.95 (dd, 1H, J = 12.56, 2.28 Hz), 7.72 (d, 1H, J = 7.08 Hz), 7.50-7.60 (m, 2 H), 7.37 (d, 1H, J = 8.80 Hz), 7.26 (t, 1H, J = 8.80 Hz), 7.05-7.15 (m, 2 H), 6.28 (d, 1H, J = 7.08 Hz), 6.09 (dd, 2H, J = 34.52, 10.56), 4.16 (q, 1H, J = 7.32 Hz), 1.47 (d, 3H, J = 7.28 Hz); MS (ESI$^+$) m/z 570 (M + H)$^+$. |

TABLE 1-continued

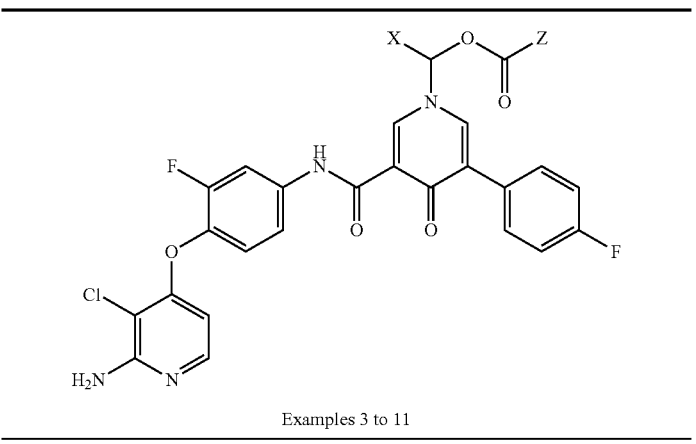

Examples 3 to 11

| Example No. | X | Z | Analytical Data |
|---|---|---|---|
| 4 | H | (1-amino-2-methylpropyl) | 1H NMR(CD3OD) δ 12.80 (br s, 1 H), 8.96 (d, 1H, J = 2.24 Hz), 8.24 (d, 1H, J = 2.52 Hz), 8.07 (dd, 1H, J = 12.84, 2.52 Hz), 7.82 (d, 1H, J = 7.04 Hz), 7.62-7.70 (m, 2H), 7.50 (d, 1H, J = 8.80 Hz), 7.37 (t, 1H, J = 8.56 Hz), 7.20-7.30 (m, 2H), 6.37 (d, 1H, J = 6.80 Hz), 6.26 (s, 2H), 4.14 (d, 1H, J = 4.52 Hz), 2.32-2.42 (m, 1H), 1.07 (d, 6H, J = 6.80 Hz); MS (ESI+) m/z 598 (M + H)+. |
| 5 | H | (1-amino-3-methylbutyl) | $^1$H NMR (CD$_3$OD) δ 12.85 (br s, 1 H), 8.95 (d, 1H, J = 2.28 Hz), 8.23 (d, 1H, J = 2.28 Hz), 8.07 (dd, 1H, J = 12.60, 2.30 Hz), 7.82 (d, 1H, J = 7.04 Hz), 7.65-7.70 (m, 2H), 7.45 (d, 1H, J = 8.80 Hz), 7.37 (t, 1H, J = 8.80 Hz), 7.18-7.28 (m, 2H), 6.36 (d, 1H, J = 7.04 Hz), 6.23 (dd, 2H, J = 22.40, 10.56 Hz), 4.21 (t, 1H, J = 6.28 Hz), 1.82-1.92 (m, 1H), 1.70-1.80 (m, 2H), 0.99 (t, 6H, J = 3.28 Hz); MS (ESI+) m/z 612 (M + H)+. |
| 6 | H | (piperidin-3-yl) | $^1$H NMR (CD$_3$OD) δ 12.89 (br s, 1 H), 8.92 (d, 1H, J = 2.28 Hz), 8.22 (d, 1H, J = 2.52 Hz), 8.07 (dd, 1H, J = 12.40, 2.30 Hz), 7.81 (d, 1H, J = 7.04 Hz), 7.60-7.70 (m, 2H), 7.48 (d, 1H, J = 5.32 Hz), 7.36 (t, 1H, J = 8.56 Hz), 7.15-7.28 (m, 2H), 6.33 (d, 1H, J = 7.08 Hz), 6.11 (s, 2H), 3.45-3.55 (m, 3H), 2.95-3.10 (m, 2H), 2.10-2.25 (m, 1H), 1.75-2.00 (m, 3H); MS (ESI+) m/z 610 (M + H)+. |
| 7 | H | (pyrrolidin-3-yl) | $^1$H NMR (CD$_3$OD) δ 12.85 (br s, 1H), 8.94 (d, 1H, J = 2.24 Hz), 8.23 (d, 1H, J = 1.76 Hz), 8.07 (dd, 1H, J = 12.84, 2.00 Hz), 7.83 (d, 1H, J = 7.04 Hz), 7.60-7.70 (m, 2H), 7.49 (d, 1H, J = 8.80 Hz), 7.38 (t, 1H, J = 8.56 Hz), 7.20-7.30 (m, 2 H), 6.39 (d, 1H, J = 6.80 Hz), 6.21 (dd, 2H, J = 42.56, 10.60 Hz), 4.57 (t, 1H, J = 9.15 Hz), 3.37-3.47 (m, 2H), 2.44-2.54 (m, 1H), 2.17-2.27 (m, 1H), 2.06-2.16 (m, 2H); MS (ESI+) m/z 596 (M + H)+. |
| 8 | H | (pyrrolidin-3-yl) | $^1$H NMR (CD$_3$OD) δ 12.80 (br s, 1H), 8.81 (d, 1H, J = 2.28 Hz), 8.10 (s, 1H), 7.95 (d, 1H, J = 10.56 Hz), 7.71 (d, 1H, J = 7.04 Hz), 7.50-7.60 (m, 2H), 7.36 (d , 1H, J = 8.56 Hz), 7.26 (t, 1H, J = 8.56 Hz), 7.00-7.15 (m, 2H), 6.26 (d, 1H, J = 7.04 Hz), 6.00 (dd, 2H, J = 14.84, 10.56 Hz), 3.45-3.55 (m, 1H), 3.30-3.40 (m, 2H), 3.15-3.30 (m, 2H), 2.20-2.35 (m, 1H), 2.10-2.20 (m, 1H); MS (ESI+) m/z 596 (M + H)+. |

TABLE 1-continued

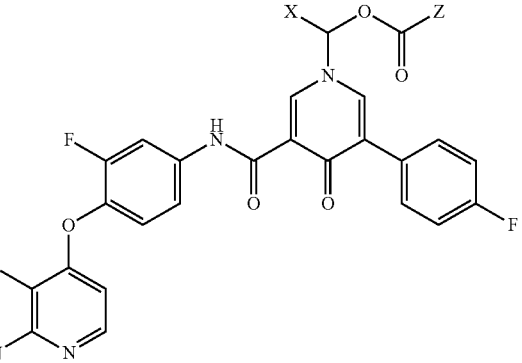

Examples 3 to 11

| Example No. | X | Z | Analytical Data |
|---|---|---|---|
| 9 | H | 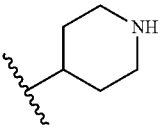 | $^1$H NMR (CD$_3$OD) δ 12.90 (br s, 1H), 8.92 (d, 1H, J = 2.24 Hz), 8.22 (d, 1H, J = 2.28 Hz), 8.09 (dd, 1H, J = 12.84, 2.24 Hz), 7.82 (d, 1H, J = 7.04 Hz), 7.60-7.75 (m, 2H), 7.48 (d, 1H, J = 8.60 Hz), 7.38 (t, 1H, J = 8.56 Hz), 7.15-7.30 (m, 2H), 6.38 (d, 1H, J = 7.04 Hz), 6.10 (s, 2H), 3.35-3.50 (m, 2H), 3.00-3.20 (m, 2H), 2.80-3.00 (m, 1H), 2.10-2.30 (m, 2H), 1.75-2.00 (m, 2H); MS (ESI$^+$) m/z 610 (M + H)$^+$. |
| 10 | Me | 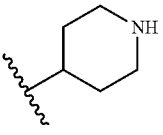 | $^1$H NMR (CD$_3$OD) δ 12.85 (br s, 1H), 8.81 (d, 1H, J = 2.52 Hz), 8.13 (d, 1H, J = 2.52 Hz), 7.97 (d, 1H, J = 12.60 Hz), 7.71 (d, 1H, J = 7.08 Hz), 7.50-7.60 (m, 2H), 7.38 (d, 1H, J = 8.60 Hz), 7.25 (t, 1H, J = 8.80 Hz), 7.05-7.15 (m, 2 H), 6.64 (q, 1H, J = 6.04 Hz), 6.26 (d, 1H, J = 7.04 Hz), 3.20-3.35 (m, 2H), 2.90-3.05 (m, 2H), 2.70-2.85 (m, 1H), 2.05-2.20 (m, 2H), 1.65-1.85 (m, 5H); MS (ESI$^+$) m/z 624 (M + H)$^+$. |
| 11 | Me | 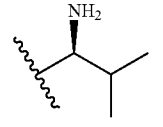 | $^1$H NMR (CD$_3$OD) δ 12.92 (br s, 1H), 8.97 (d, 1H, J = 6.04 Hz), 8.28 (d, 1H, J = 21.12 Hz), 8.08 (d, 1H, J = 12.32 Hz), 7.82 (d, 1H, J = 7.08 Hz), 7.60-7.75 (m, 2H), 7.40 (d, 1H, J = 8.20 Hz), 7.38 (t, 1H, J = 8.80 Hz), 7.20-7.30 (m, 2H), 6.64 (q, 1H, J = 6.28 Hz), 6.36 (d, 1H, J = 6.80 Hz), 4.08-4.20 (m, 1H), 2.25-2.45 (m, 1H), 2.25-2.45 (m, 1H), 1.97 (d, 3H, J = 5.28 Hz), 0.85-1.15 (m, 5H); MS (ESI$^+$) m/z 612 (M + H)$^+$. |

Example 12

(3-(4-(2-Amino-3-chloropyridin-4-yloxy)-3-fluorophenylcarbamoyl)-5-(4-fluorophenyl)-4-oxopyridin-1(4H)-yl)methyl 1-methylpiperidine-4-carboxylate

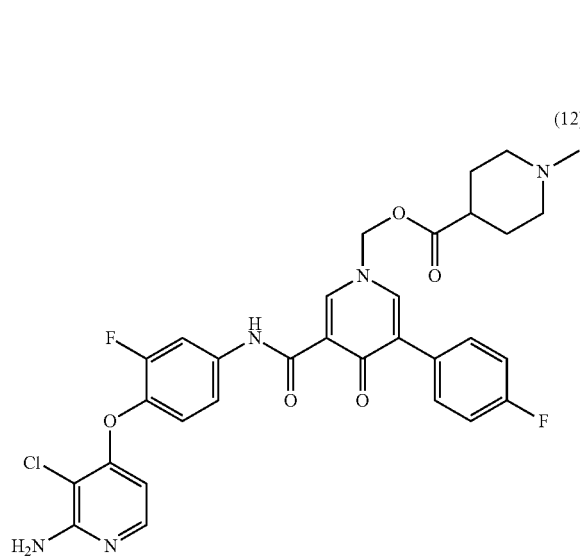

(12)

Preparation 12A: N-(4-(2-(Benzhydrylamino)-3-chloropyridin-4-yloxy)-3-fluorophenyl)-5-(4-fluorophenyl)-4-oxo-1,4-dihydropyridine-3-carboxamide

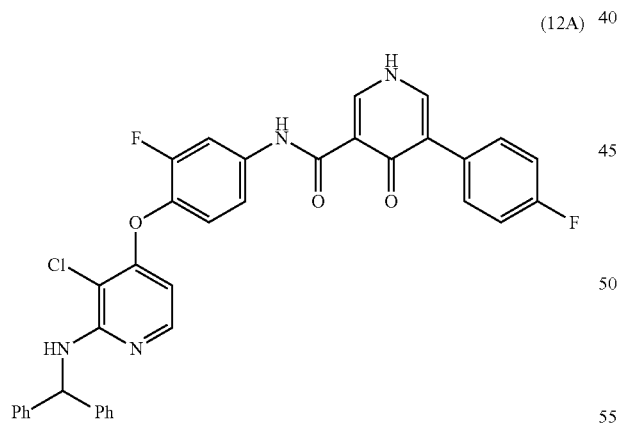

(12A)

To a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (Preparation 1G, 127 mg, 0.2 mmol) in EtOH (5 mL) and THF (5 mL) at 0° C., was added NaBH$_4$ (300 mg, 7.93 mmol). The mixture was stirred at 0° C. for 3 h, and then at rt overnight. The reaction was quenched with water, extracted with DCM, and dried over MgSO$_4$. After filtration and concentration in vacuo, 120 mg of the desired material was obtained as a white solid. MS (ESI$^+$) m/z 635 (M+H)$^+$.

Preparation 12B: 4-(3-(4-(2-(Benzhydrylamino)-3-chloropyridin-4-yloxy)-3-fluorophenylcarbamoyl)-5-(4-fluorophenyl)-4-oxopyridin-1(4H)-yl)methyl 1-tert-butyl piperidine-1,4-dicarboxylate

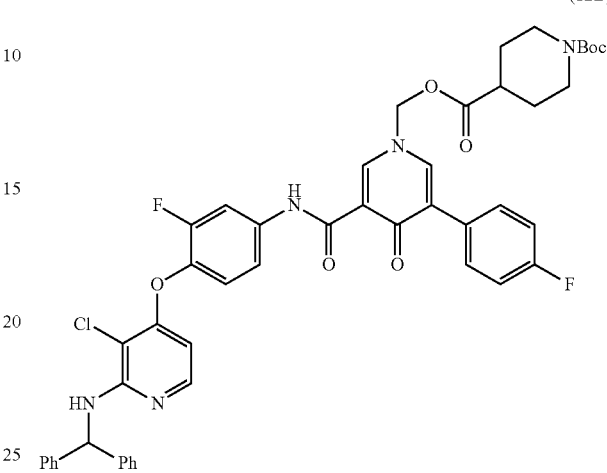

(12B)

A mixture of N-(4-(2-(benzhydrylamino)-3-chloropyridin-4-yloxy)-3-fluorophenyl)-5-(4-fluorophenyl)-4-oxo-1,4-dihydropyridine-3-carboxamide (120 mg, 0.189 mmol), K$_2$CO$_3$ (104 mg, 0.756 mmol) and 1-tert-butyl 4-chloromethyl piperidine-1,4-dicarboxylate (157 mg, 0.567 mmol) in DMF (2 mL) was stirred at rt for 3 h. The reaction mixture was then diluted with DCM and the solid that formed was filtered off. The residue was washed with sat. aq. KH$_2$PO$_4$ solution. The organic layer was dried over MgSO$_4$ and the desired product was purified by flash column chromatography (SiO$_2$, eluting with a DCM/EtOAc gradient) to give the desired compound (145 mg) as a white solid. MS (ESI$^+$) m/z 876 (M+H)$^+$.

Preparation 12C: (3-(4-(2-(Benzhydrylamino)-3-chloropyridin-4-yloxy)-3-fluorophenylcarbamoyl)-5-(4-fluorophenyl)-4-oxopyridin-1(4H)-yl)methyl piperidine-4-carboxylate

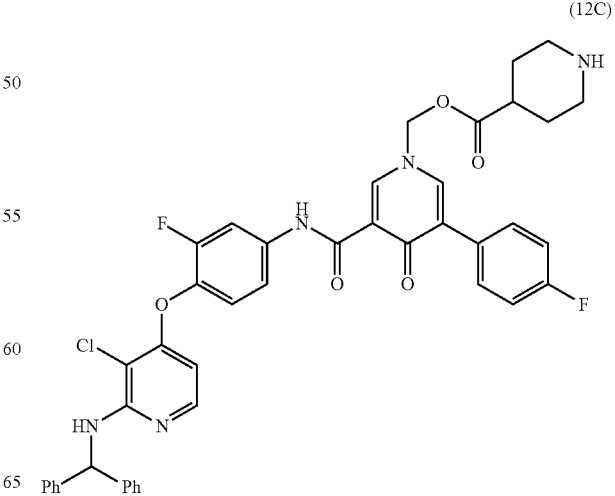

(12C)

To a solution of 4-(3-(4-(2-(benzhydrylamino)-3-chloro-pyridin-4-yloxy)-3-fluorophenylcarbamoyl)-5-(4-fluorophenyl)-4-oxopyridin-1(4H)-yl)methyl 1-tert-butyl piperidine-1,4-dicarboxylate (135 mg, 0.154 mmol) in DCM (5 mL) at rt, was added HCl (4 N in dioxane, 1 mL). The reaction mixture was stirred at rt for 3 h. The solvents were removed in vacuo and the resulting residue was purified by preparative—HPLC to give the desired product (128 mg) as a white solid. MS (ESI⁺) m/z 776 (M+H)⁺.

Preparation 12D: (3-(4-(2-(Benzhydrylamino)-3-chloropyridin-4-yloxy)-3-fluorophenylcarbamoyl)-5-(4-fluorophenyl)-4-oxopyridin-1(4H)-yl)methyl 1-methylpiperidine-4-carboxylate

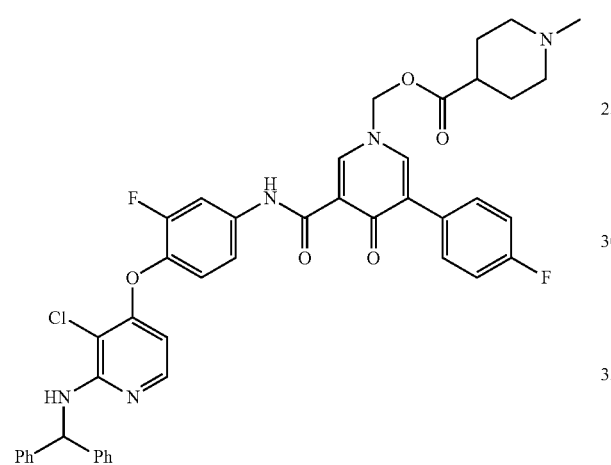

To a mixture of (3-(4-(2-(benzhydrylamino)-3-chloropyridin-4-yloxy)-3-fluorophenylcarbamoyl)-5-(4-fluorophenyl)-4-oxopyridin-1(4H)-yl)methyl piperidine-4-carboxylate (60 mg, 0.077 mmol), formaldehyde (37% in water, 0.08 mL, 0.077 mmol) and acetic acid (0.03 mL, 0.077) in acetonitrile (2 mL) at rt was added, NaCNBH₃ (50 mg, 0.8 mmol). The resulting mixture was stirred for 30 min. The solvent was removed in vacuo and the crude product residue was used directly in the next step without further purification.

Example 12

Preparation (12E) (0.077 mmol) was treated with TFA (3 mL) at rt for 30 min. The volatiles were removed in vacuo and the resulting residue was purified by preparative-HPLC to afford the title compound (32 mg) as a white solid. ¹H NMR (CD₃OD) δ 12.91 (br s, 1H), 8.92 (d, 1H, J=2.52 Hz), 8.21 (d, 1H, J=2.00 Hz), 8.08 (dd, 1H, J=13.08, 2.04 Hz), 7.83 (d, 1H, J=7.08 Hz), 7.62-7.70 (m, 2H), 7.48 (d, 1H, J=8.80 Hz), 7.39 (t, 1H, J=8.56 Hz), 7.20-7.28 (m, 2H), 6.41 (d, 1H, J=6.28 Hz), 6.10 (s, 2H), 3.50-3.60 (m, 2H), 3.00-3.10 (m, 2H), 2.89 (s, 3H), 2.80-2.89 (m, 1H), 2.25-2.35 (m, 2H), 1.80-1.90 (m, 2H); MS (ESI⁺) m/z 624 (M+H)⁺.

Example 13

(3-(4-(2-Amino-3-chloropyridin-4-yloxy)-3-fluorophenylcarbamoyl)-5-(4-fluorophenyl)-4-oxopyridin-1(4H)-yl)methyl dihydrogen phosphate, bis-ethanolamine salt

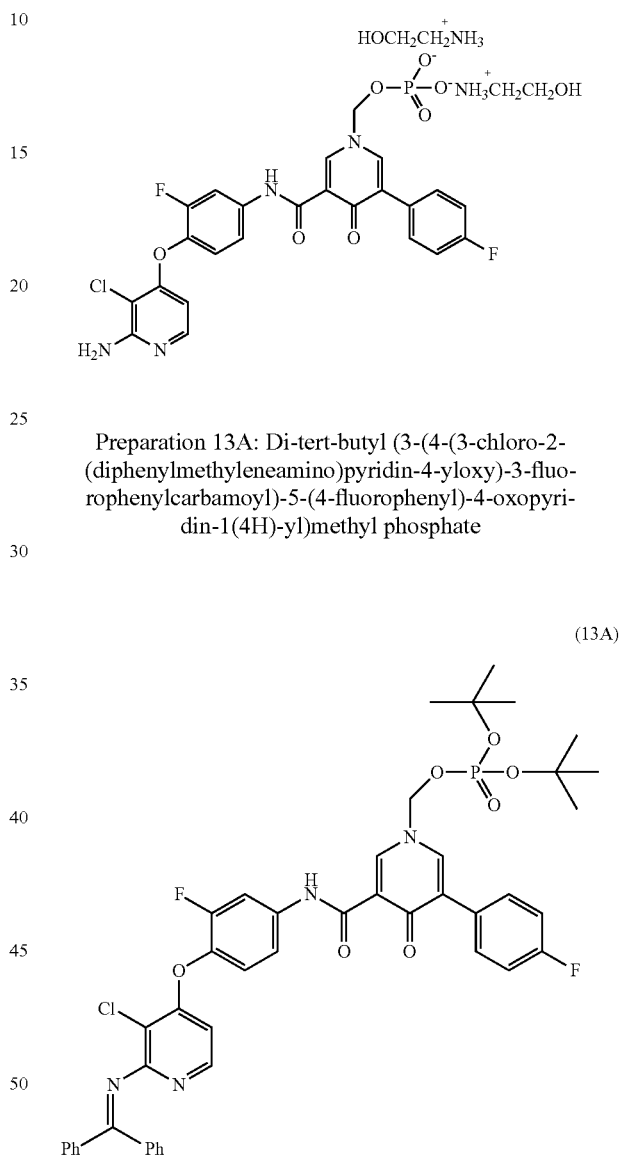

Preparation 13A: Di-tert-butyl (3-(4-(3-chloro-2-(diphenylmethyleneamino)pyridin-4-yloxy)-3-fluorophenylcarbamoyl)-5-(4-fluorophenyl)-4-oxopyridin-1(4H)-yl)methyl phosphate (13A)

To a solution of N-(4-(3-Chloro-2-(diphenylmethyleneamino)pyridin-4-yloxy)-3-fluorophenyl)-5-(4-fluorophenyl)-4-oxo-1,4-dihydropyridine-3-carboxamide (1.0 g, 1.58 mmol) in DMF (10 mL) at room temperature were added Cs₂CO₃ (1.3 g, 3.95 mmol), potassium iodide (525 mg, 3.16 mmol) and then di-tert-butyl chloromethyl phosphate (1.2 mL, 1.90 mmol: 2.0 M in DMF). The reaction mixture was stirred at room temperature for 26 h prior to being quenched by the addition of isopropyl acetate (10 mL) and cold water (50 mL). The organics were separated and washed with water (50 mL). The solvent was swapped into isopropanol (10 mL) by continuous distillation at 86° C. The solution was cooled to 20° C. and a solid precipitated. The solid was collected by filtration and dried under vacuum at 60° C. for 12 h to give the desired product (0.98 g, 72%) as an off-white solid. MS (ESI+) m/z 856 (M+H)+.

Example 13

To a 50 mL round bottom flask was added di-tert-butyl (3-(4-(3-chloro-2-(diphenylmethyleneamino)pyridin-4-yloxy)-3-fluorophenylcarbamoyl)-5-(4-fluorophenyl)-4-oxopyridin-1(4H)-yl)methyl phosphate (4 g, 4.68 mmol) and $CH_2Cl_2$ (4 mL). The mixture was cooled to 0° C. and then trifluoroacetic acid (4 mL) was added. The reaction mixture was allowed to warm to 20° C. HPLC indicated that the di-tert-butylphosphate hydrolyzed to the acid. Water (0.4 mL) was added at 20° C. and the mixture was allowed to stir at 20° C. for 5-6 h. The mixture become a thick slurry. Toluene (20 mL) was added and then concentrated to approximately 5 mL to remove excess trifluoroacetic acid, $CH_2Cl_2$, and water. This was repeated twice. The suspension was diluted with EtOH (120 mL, 100%). To this suspension was added ethanolamine until a pH of approximately 8.1 was obtained at 20° C. The suspension becomes clear during the addition. After the addition, the solution was heated to 75° C. and square plate crystals were observed to form. The mixture was allowed to cool to 20° C. and then stirred for 24 h. The solids were removed by filtration and were washed with EtOH (100%) to afford the bis-ethanolamine salt as square-plate crystals. The solid was reslurried with EtOH (120 mL, 100%) at 75° C. with ethanolamine (~0.1 g). Rod-like needle crystals were added to the suspension and stirred at 75° C. for 7 h. The mixture was allowed to cool to 20° C. and the solids were collected by filtration to afford the bis-ethanolamine salt as large rod-like crystals. The crystals were dried at 55° C. for 14 h.

Example 14

(3-(4-(2-Amino-3-chloropyridin-4-yloxy)-3-fluorophenylcarbamoyl)-5-(4-fluorophenyl)-4-oxopyridin-1(4H)-yl)methyl dihydrogen phosphate, bis-trisamine salt (14)

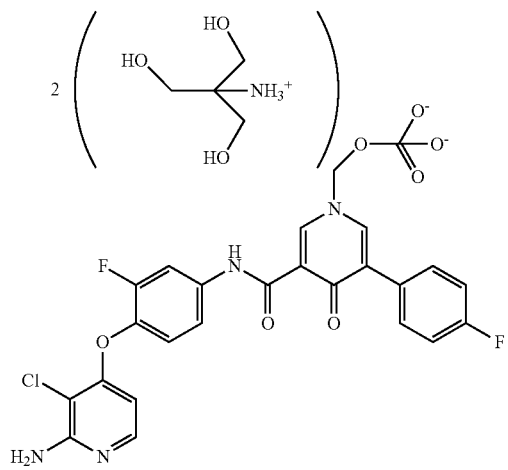

To a 50 mL round bottom flask was added di-tert-butyl (3-(4-(3-chloro-2-(diphenylmethyleneamino)pyridin-4-yloxy)-3-fluorophenylcarbamoyl)-5-(4-fluorophenyl)-4-oxopyridin-1(4H)-yl)methyl phosphate (1 g, 1.17 mmol) and $CH_2Cl_2$ (1 mL). The mixture was cooled to 0° C. and then trifluoroacetic acid (1 mL) was added. The reaction mixture was allowed to warm to 20° C. HPLC indicated that the di-tert-butylphosphate hydrolyzed to the acid. Water (0.1 mL) was added at 20° C. and the mixture was stirred at 20° C. for 6 h. The mixture became a thick slurry. Toluene (5 mL) was added and then concentrated to approximately 1 mL to remove excess trifluoroacetic acid, $CH_2Cl_2$, and water. This was repeated twice. EtOH (30 mL, 100%) was added which produced a cloudy suspension. The suspension was heated to 75° C. and concentrated aqueous Trisamine solution (2-amino-2-hydroxymethyl-1,3-propanediol) was added to produce a pH ~7.3. The solution then becomes clear and bis-trisamine seeds were added at 75° C. and the suspension was aged for 4 h at 75° C. The suspension was cooled to 20° C. and was aged for 2 h. Crystalline solids were collected by filtration and dried under vacuum at 55° C. to afford the bis-trisamine salt.

Assays

The pharmacological properties of the compound of this invention may be confirmed by a number of pharmacological assays. The exemplified pharmacological assays which follow have been carried out with the compound according to the invention and/or salts and/or prodrugs thereof.

Met Kinase Assay

Incubation mixtures employed for the Met kinase assay contain a baculovirus expressed GST-Met kinase, the synthetic substrate polyGlu:Tyr, (4:1), ATP, ATP-γ-$^{33}$P and buffer containing $Mn^{+2}$, DTT, BSA, and Tris. Reactions were incubated for 60 minutes at 30° C. and stopped by the addition of cold trichloroacetic acid (TCA) to a final concentration 8%. TCA precipitates were collected onto GF/C UniFilter plates (Packard Instrument Co., Meriden, Conn.) using a FILTER-MATE® universal harvester (Packard Instrument Co., Meriden, Conn.) and the filters are quantitated using a TopCount 96/384-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethyl sulfoxide (DMSO) and evaluated at ten concentrations, each in duplicate. The final concentration of DMSO in the assay is 1.7%. $IC_{50}$ values were derived by non-linear regression.

TABLE 2

| Reagents | Substrate Mix Final Concentration |
|---|---|
| Stock Solution | |
| Tris-HCl, (1M, pH 7.4) | 20 mM |
| $MnCl_2$ (1M) | 1 mM |
| DTT (1M) | 1 mM |
| BSA (100 mg/ml) | 0.1 mg/ml |
| $polyGlu_4$/tyr (10 mg/ml) | 0.1 mg/mL |
| ATP (1 mM) | 1 μM |
| γ-ATP (10 μCi/μl) | 0.2 μCi/ml |

TABLE 3

| Buffer | Enzyme mix |
|---|---|
| 20 ul 1M DTT | 4 ul GST/Met enzyme(3.2 mg/ml) = 10 ng/rxn |
| 200 ul 1M Tris-HCL, pH 7.4 | qs 12 ml Buffer |

TABLE 3-continued

| Buffer | Enzyme mix |
|---|---|
| 20 ul 100 mg/ml BSA | |
| qs 20 ml H$_2$0 | |

GTL-16 Gastric Carcinoma Proliferation Assay

Inhibition of GTL-16 cell growth was assessed by a MTS assay using a CELLTITER 96® Aqueous Non-Radioactive Proliferation Assay kit from Promega. The kit is composed of solutions of a novel tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate, PMS). In this colormetric assay, the conversion of MTS into aqueous, soluble formazan is accomplished by dehydrogenase enzymes found in metabolically active cells. The quantity of formazan product as measured by its absorbance at 490 nm is directly proportional to the number of living cells in culture.

GTL-16 cells were inoculated into 96 well microtiter plates in 0.5% fetal calf serum and incubated at 37° C., 5% CO$_2$, 95% air and 100% relative humidity for 24 h prior to addition of a compound. At the time of drug treatment, one plate of the cell line was processed using the above kit to represent a measurement of the cell population at the time of drug addition. Following drug treatment, the plates were incubated for an additional 72 h before processing, and measuring cell populations. Each compound was tested at 8 different concentrations in triplicate, as was the untreated control sample. Growth inhibition of 50% (IC$_{50}$) is calculated by analysis of the data in Excel that uses a 4 parameter logistic equation with data fitted using the Levenburg Marquardt algorithm VEGFR-2 Kinase Assay

| Reagents | Final Concentration |
|---|---|
| Stock Solution | VEGFR-2 |
| Tris pH 7.0 | 20 mM |
| BSA 10 mg/ml | 25 µg/ml |
| MnCl$_2$ (1M) | 1.5 mM |
| DTT (1M) | 0.5 mM |
| Enzyme Stock in 10% glycerol (1 mg/ml) | 7.5 ng/rxn |
| Poly glu/tyr (10 mg/ml) | 75 µg/ml |
| ATP (1 mM) | 2.5 µM |
| γ-ATP (10 µCi/µl) | 0.5 µCi/ml |

Incubation mixtures employed for the VEGFR-2 assay contain the synthetic substrate poly glu/tyr, (4:1), ATP, ATP-γ-$^{33}$P and buffer containing Mn$^{+2}$, DTT, BSA, and Tris buffer. The reaction is initiated by addition of enzyme and after 60 minutes at room temperature is terminated by the addition of 30% TCA to a final concentration of 15% TCA. Inhibitors are brought to 10 mM in 100% DMSO. Assays are prepared in a 96 well format in quadruplicate. Compounds are diluted 1:500 in 100% DMSO and then 1:10 in water for a final DMSO concentration of 10%. Aliquots (10 µL) are added to rows B-H in a 96 well format of 10% DMSO. The compound (20 µl) is added to row A at a concentration 5 fold higher than running conditions. Aliquots (10 µL) are transferred to each row followed by six serial dilutions with mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FILTER-MATE® harvester. Activity is determined by quantitating the incorporated radioactivity using a Packard TopCount Microplate Scintillation Counter following the addition of Microscint-20 cocktail into each dried well of the UniFilter microplates.

Table 4 shows the activities of Example 1 and Compounds A and B in the MET kinase assay, the VEGFR-2 assay, and/or the GTL-16 assay. The preparations of Compounds A and B are disclosed in U.S. Patent Publication 2005/0245530 in examples 56 and 101, respectively.

TABLE 4

| | MET Kinase IC$_{50}$ (nM) | GTL-16 IC$_{50}$ (nM) | VEGFR-2 IC$_{50}$ (nM) |
|---|---|---|---|
| Example 1 | 1.7 | 39 | 15 |
| Compound A | 160 | 5400 | — |
| Compound B | 4.8 | 170 | 40 |

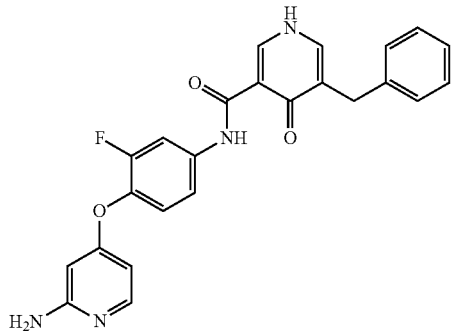

Compound A

Compound B

Compound A: N-(4-(2-Aminopyridin-4-yloxy)-3-fluorophenyl)-5-benzyl-4-oxo-1,4-dihydropyridine-3-carboxamide, trifluoroacetic acid salt.

Compound B: N-(4-(2-Aminopyridin-4-yloxy)-3-fluorophenyl)-1-(4-fluorophenyl)-2-oxo-1,2-dihydropyridine-3-carboxamide, hydrochloride salt.

In Vivo Efficacy Determination

N-(4-(2-Amino-3-chloropyridin-4-yloxy)-3-fluorophenyl)-5-(4-fluorophenyl)-4-oxo-1,4-dihydropyridine-3-carboxamide (Example 1) and (3-(4-(2-amino-3-chloropyridin-4-yloxy)-3-fluorophenylcarbamoyl)-5-(4-fluorophenyl)-4-oxopyridin-1(4H)-yl)methyl dihydrogen phosphate (Example 2) were evaluated for in vivo efficacy against the GTL-16 human gastric tumor xenograft model. Example 2 is a prodrug of Example 1. As illustrated in FIG. 1, Example 1 and Example 2 were active as defined by greater than 50% tumor growth inhibition (TGI) for at least one tumor doubling time in the GTL-16 gastric carcinoma model. No overt toxicity was observed at any of these dose levels when administered once daily for a duration of 14 days. In this study, equimolar concentrations of Example 1 (25 mg/kg of Example 1 and 31.2 mg/kg of Example 2) resulted in complete tumor stasis.

Figure 2:
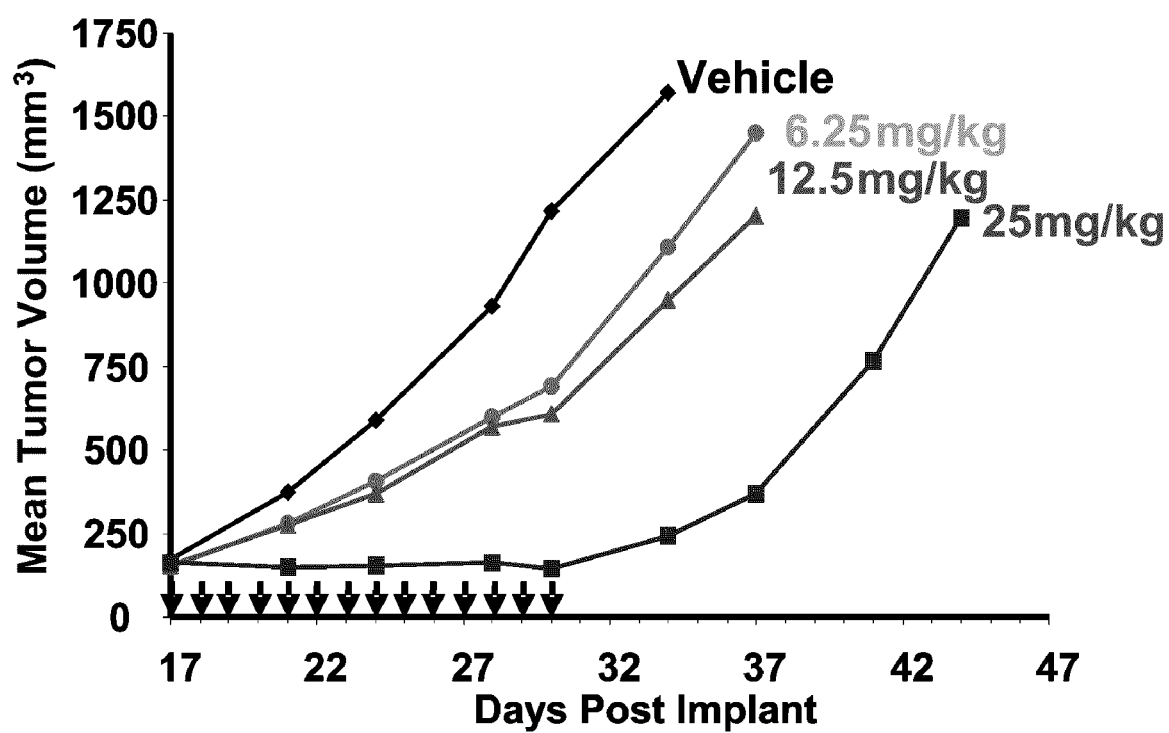
FIG. 2 shows antitumor activity of Example 1 dosed orally once daily for 14 days (arrows denote dosing) at 6.25 mpk (mg/kg), 12.5 mpk, and 25 mpk against U87 glioblastoma xenografts.
Figure 3:
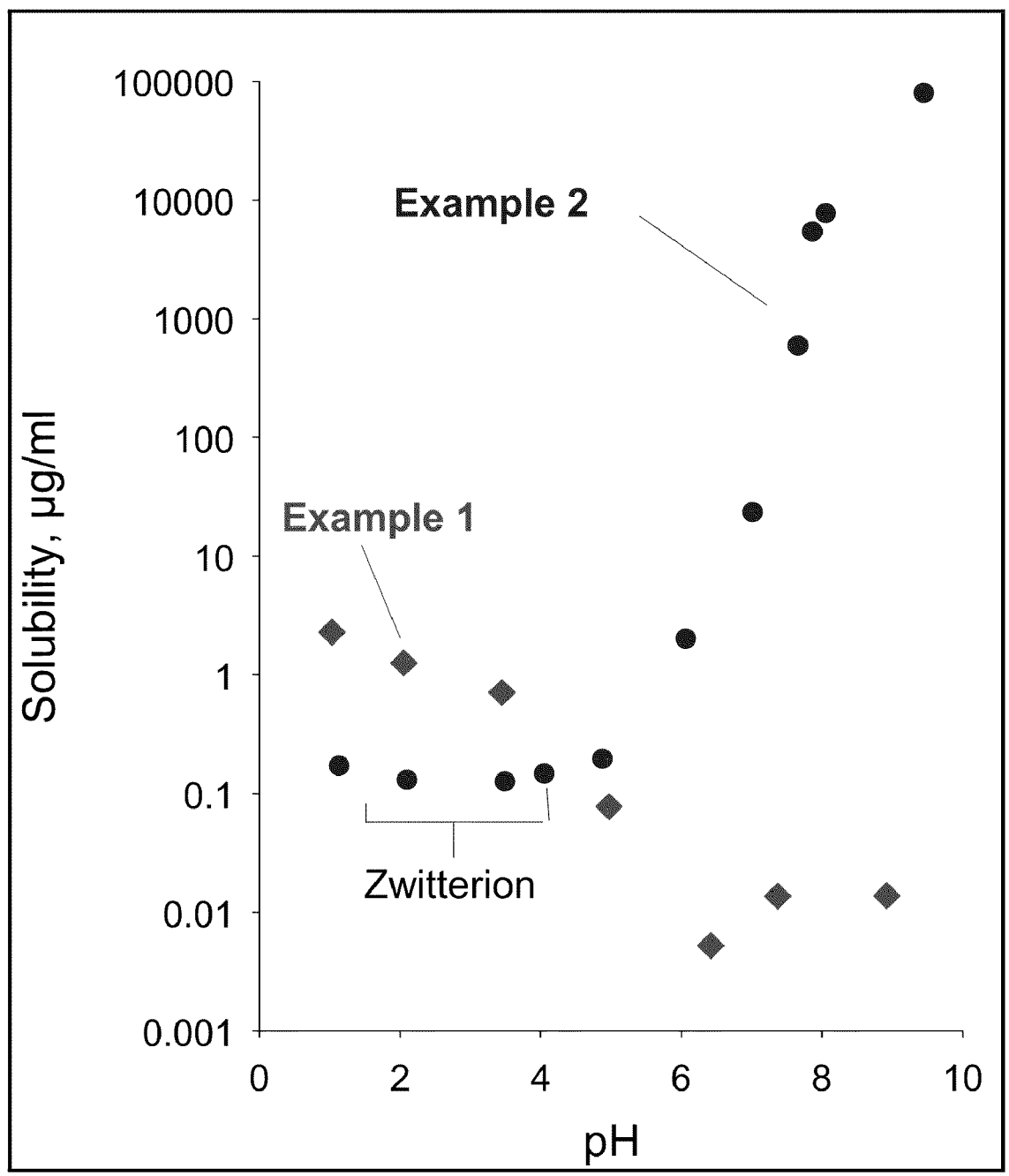
FIG. 3 shows the pH-solubility profiles of Example 1 and Example 2.

Example 1 was also tested in the U87 glioblastoma model, a Met driven tumor based on an HGF autocrine mechanism of Met activation. As demonstrated in FIG. 2, complete tumor stasis was observed at 25 mg/kg, similar to the activity observed against GTL-16 tumor xenografts.

What is claimed is:

1. A compound having the following Formula (I):

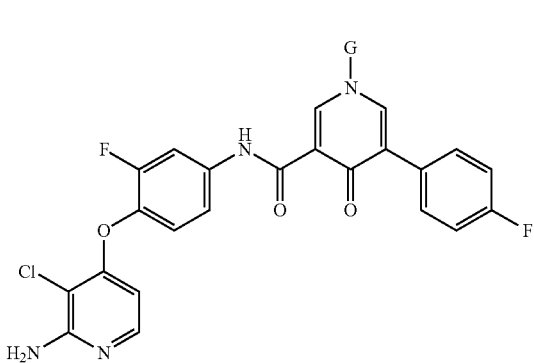

(I)

or a salt thereof, wherein:
G is H, —CHX—OP(=O)(OH)$_2$, or —CHX—OC(=O)Z;
X is H or alkyl optionally substituted with one or more of OH, halogen, cyano, and/or —NR$^1$R$^2$;
Z is alkyl, cycloalkyl, aryl, or heterocyclo optionally substituted with one or more of alkyl, OH, halogen, cyano, and/or —NR$^3$R$^4$; and
R$^1$, R$^2$, R$^3$, and R$^4$ are independently H and/or alkyl.

2. The compound of claim 1 or a salt thereof, wherein: G is H.

3. The compound of claim 1 or a salt thereof:
G is —CHX—OP(=O)(OH)$_2$; and
X is H or C$_1$-C$_2$alkyl optionally substituted with one or more of OH, halogen, cyano, and/or —NR$^1$R$^2$.

4. The compound according to claim 3 or a salt thereof, wherein:
X is H or methyl.

5. A compound having the formula:

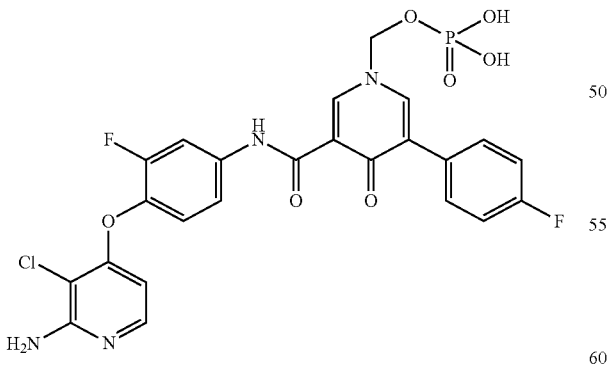

or a salt thereof.

6. The compound according to claim 1 or a salt thereof, wherein:
G is —CHX—OC(=O)Z;
X is H, C$_1$-C$_2$alkyl optionally substituted with one or more of OH, halogen, cyano, and/or —NR$^1$R$^2$;

Z is C$_1$-C$_6$alkyl or 5- to 6-membered heterocyclo comprising one nitrogen heteroatom, optionally substituted with one or more of alkyl, OH, halogen, cyano, and/or —NR$^3$R$^4$; and
R$^1$, R$^2$, R$^3$, and R$^4$ are independently H and/or C$_1$-C$_4$alkyl.

7. The compound according to claim 6 or a salt thereof, wherein X is H or methyl.

8. The compound according to claim 7 or a salt thereof, wherein G is:

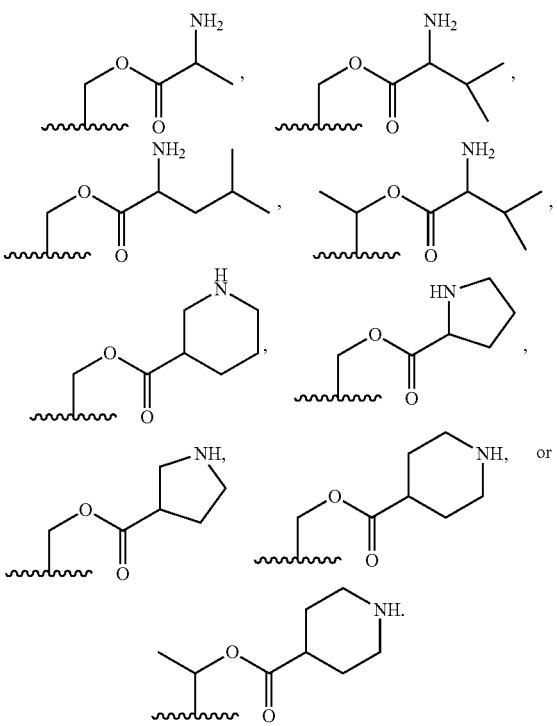

9. The compound according to claim 1 or a salt thereof, wherein said compound is:
N-(4-(2-Amino-3-chloropyridin-4-yloxy)-3-fluorophenyl)-5-(4-fluorophenyl)-4-oxo-1,4-dihydropyridine-3-carboxamide (1);
(3-(4-(2-Amino-3-chloropyridin-4-yloxy)-3-fluorophenylcarbamoyl)-5-(4-fluorophenyl)-4-oxopyridin-1(4H)-yl)methyl dihydrogen phosphate (2);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-aminopropanoate (3);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-amino-3-methylbutanoate (4);
(S)-(3-(4-(2-amino-3-chloropyridin-4-yloxy)-3-fluorophenylcarbamoyl)-5-(4-fluorophenyl)-4-oxopyridin-1(4H)-yl)methyl 2-amino-4-methylpentanoate (5);
(3-(4-(2-amino-3-chloropyridin-4-yloxy)-3-fluorophenylcarbamoyl)-5-(4-fluorophenyl)-4-oxopyridin-1(4H)-yl)methyl piperidine-3-carboxylate (6);
(S)-(3-(4-(2-amino-3-chloropyridin-4-yloxy)-3-fluorophenylcarbamoyl)-5-(4-fluorophenyl)-4-oxopyridin-1(4H)-yl)methylpyrrolidine-2-carboxylate (7);
(S)-(3-(4-(2-amino-3-chloropyridin-4-yloxy)-3-fluorophenylcarbamoyl)-5-(4-fluorophenyl)-4-oxopyridin-1(4H)-yl)methylpyrrolidine-3-carboxylate (8);

(3-(4-(2-amino-3-chloropyridin-4-yloxy)-3-fluorophenylcarbamoyl)-5-(4-fluorophenyl)-4-oxopyridin-1(4H)-yl)methyl piperidine-4-carboxylate (9);

1-(3-(4-(2-amino-3-chloropyridin-4-yloxy)-3-fluorophenylcarbamoyl)-5-(4-fluorophenyl)-4-oxopyridin-1(4H)-yl)ethyl piperidine-4-carboxylate (10);

(2S)-1-(3-(4-(2-amino-3-chloropyridin-4-yloxy)-3-fluorophenylcarbamoyl)-5-(4-fluorophenyl)-4-oxopyridin-1(4H)-yl)ethyl 2-amino-3-methylbutanoate (11); or (3-(4-(2-Amino-3-chloropyridin-4-yloxy)-3-fluorophenylcarbamoyl)-5-(4-fluorophenyl)-4-oxopyridin-1(4H)-yl)methyl 1-methylpiperidine-4-carboxylate (12).

10. A pharmaceutical composition comprising at least one compound according to claim 1 or a pharmaceutically acceptable salt thereof; and a pharmaceutically acceptable carrier or diluent.

11. The pharmaceutical composition according to claim 10, wherein said at least one compound is:

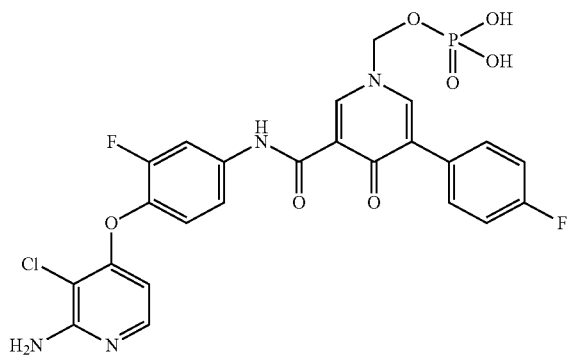

or a pharmaceutically acceptable salt thereof.

12. The compound according to claim 2 or a salt thereof, wherein said compound is a HCl salt.

13. The compound according to claim 5, having the formula:

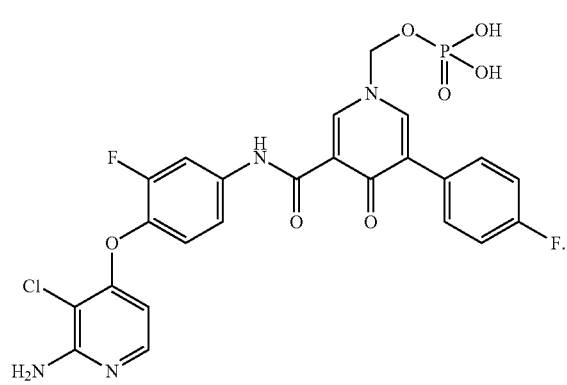

14. The compound according to claim 5 or salt thereof, wherein said salt is a pharmaceutically acceptable salt.

15. The compound according to claim 14 or a salt thereof, wherein said salt is a bis-ethanolamine salt.

16. The compound according to claim 14 or a salt thereof, wherein said salt is a bis-trisamine salt.

17. A compound or a salt thereof, wherein said compound is:

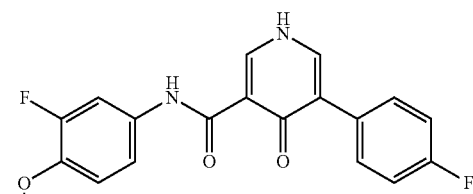

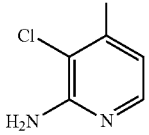

or

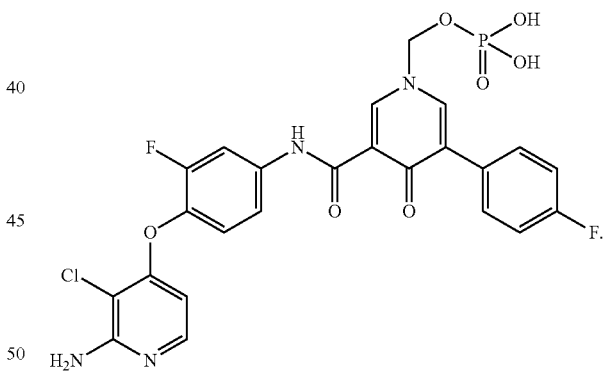

* * * * *

UNITED STATES PATENT AND TRADEMARK OFFICE
CERTIFICATE OF CORRECTION

PATENT NO. : 8,124,768 B2
APPLICATION NO. : 12/863697
DATED : February 28, 2012
INVENTOR(S) : Borzilleri et al.

It is certified that error appears in the above-identified patent and that said Letters Patent is hereby corrected as shown below:

In the Claims:

Col. 46, line 64, claim 9, delete "methylpyrrolidine" and insert -- methyl pyrrolidine --, therefor.

Col. 46, line 67, claim 9, delete "methylpyrrolidine" and insert -- methyl pyrrolidine --, therefor.

Signed and Sealed this
Tenth Day of July, 2012

David J. Kappos
*Director of the United States Patent and Trademark Office*